US006495526B2

(12) United States Patent
Gyuris et al.

(10) Patent No.: US 6,495,526 B2
(45) **Date of Patent: *Dec. 17, 2002**

(54) INHIBITORS OF CELL-CYCLE PROGRESSION AND USES RELATED THERETO

(75) Inventors: Jeno Gyuris, Winchester, MA (US); Lou Lamphere, Boston, MA (US); David H. Beach, Huntington Bay, NY (US)

(73) Assignee: GPC Biotech, Inc., Waltham, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 49 days.

(21) Appl. No.: 08/902,572

(22) Filed: Jul. 29, 1997

(65) Prior Publication Data

US 2002/0068706 A1 Jun. 6, 2002

Related U.S. Application Data

(63) Continuation-in-part of application No. 08/589,981, filed on Jan. 23, 1996, now Pat. No. 5,672,508.

(51) Int. Cl.[7] ........................ A61K 48/00; C07H 21/04

(52) U.S. Cl. .................... 514/44; 536/23.4; 536/23.72; 536/24.1

(58) Field of Search ............................ 536/23.4, 23.72, 536/24.1

(56) References Cited

U.S. PATENT DOCUMENTS

| | | | | | |
|---|---|---|---|---|---|
| 4,902,505 A | * | 2/1990 | Pardridge et al. | ............ | 424/85 |
| 5,136,022 A | | 8/1992 | Brown et al. | | |
| 5,596,079 A | * | 1/1997 | Smith et al. | ............... | 530/328 |
| 5,616,559 A | | 4/1997 | Androphy et al. | | |
| 5,625,031 A | * | 4/1997 | Webster et al. | ............ | 530/300 |
| 5,652,122 A | * | 7/1997 | Frankel et al. | ............ | 435/69.7 |
| 5,686,264 A | * | 11/1997 | Gaynor et al. | ............ | 435/69.1 |
| 5,723,313 A | * | 3/1998 | Sherr et al. | ............... | 435/69.1 |
| 6,316,003 B1 | | 11/2001 | Frankel et al. | | |

FOREIGN PATENT DOCUMENTS

| | | | | |
|---|---|---|---|---|
| WO | WO93/20834 | * 10/1993 | ................. | 514/44 |
| WO | WO 95 28483 A | 10/1995 | | |
| WO | WO 96/31534 A | 10/1996 | | |
| WO | WO 97/11174 A | 3/1997 | | |

OTHER PUBLICATIONS

Verma et al. Gene therapy—promises, problems and prospects. Nature vol. 389:239–242, Aug. 19, 1997.*

Orkin et al. Report and recommendations of the panel to assess the NIH investment in research on gene therapy, Dec. 7, 1995.*

Apodaca et al. Transcytosis of placenta alkaline phosphatase–polymeric immunoglobulin receptor fusion proteins is regulated by mutations of Ser. 664. J. Biol. Chemistry vol. 268(5):23712–23719, Nov. 1993.*

Cujec et al. The HIV transactivator TAT binds to the CDK–acitvating kinase and activates the phosphorylation of the carboxy–terminal domain of RNA polymerase II. Genes and Development vol. 11:2645–2657, Oct. 1997.*

Perez et al. Antennapedia homeobox as a signal for teh cellular internalization and nuclear addressing of a small exogenous peptide. J. Cell Science vol. 102:717–722, Jun. 1992.*

Frankel, A.D. et al. "Cellular uptake of the Tat protein from human immunodeficiency virus" *Cell*, 55, Dec. 23, 1988, 1189–1193.

Ezhevsky, S. A. et al. "Hypo–phosphorylation of the retinoblastoma protein by cyclin D: Cdk4/6 complexes results in active pRb" *Proc. Natl. Acad. Sci U.S.A.*, 94, Sep. 1997, 10699–10704.

Bonifaci et al. Nuclear translocation of an exogenous fusion protein containing HIV Tat requires unfolding. *AIDS* 9, 995–1000 (1995).

Luo, Y. et al. "Cell–Cycle Inhibition by Independent CDK and PCNA Binding Domains in P21 CIP1" *Nature*, vol. 375, May 11, 1995, pp. 159–161.

Bonfanti M. et al., "p21 WAF1–derived Peptides Linked to an Internalization Peptide Inhibit Human Cancer Cell Growth" *Cancer Research*, vol. 57, Apr. 15, 1997, pp. 1442–1446.

MacLachlan T. K., et al. "Cyclins, Cyclin–Dependent Kinases, and CDK Inhibitors: Implications in Cell Cycle Control and Cancer" *Nishinihon Journal of Urology*, vol. 5, Jan. 1, 1995, pp. 127–156.

Bjornsson T. D. et al. "Acidic Fibroblast Growth Factor Promotes Vascular Repair" *Proceedings of the National Academy of Sciences U.S.A.*, vol. 88, Oct. 1991, pp. 8651–8655.

Kashanchi et al. Direct interaction of human TFIID with the HIV transactivator Tat. Nature. vol. 367:295–299, Jan. 1994.*

Feaver et al. Relationship of CDK–actvating kinase and RNA Polymerase II CTD kinase TFIIH/TFIIK. Cell:1103–1109, Oct. 1994.*

Marshall, E. Gene therapy's growing pains. Science. vol. 269:1050–1055, Aug. 1995.*

Anderson, WF. Human gene therapy. Nature, vol. 392:25–30, Apr. 1998.*

* cited by examiner

*Primary Examiner*—Terry McKelvey
*Assistant Examiner*—William Sandals
(74) *Attorney, Agent, or Firm*—Ropes & Gray

(57) ABSTRACT

The present invention pertains to novel inhibitors of cyclin-dependent kinases (CDKs), particularly CDK/cyclin complexes, which inhibitors can be used to control proliferation and/or differentiation of cells in which the inhibitors are introduced.

42 Claims, No Drawings

INHIBITORS OF CELL-CYCLE PROGRESSION AND USES RELATED THERETO

RELATED APPLICATIONS

This application is a continuation-in-part of U.S. Ser. No. 08/589,981, entitled *Inhibitors of Cell-Cycle Progression, and Uses Related Thereto*, filed on Jan. 23, 1996 now U.S. Pat. No. 5,672,508.

BACKGROUND OF THE INVENTION

The cell division cycle is one of the most fundamental processes in biology which, in multicellular organisms, ensures the controlled generation of cells with specialized functions. Under normal growth conditions, cell proliferation is tightly regulated in response to diverse intra- and extracellular signals. This is achieved by a complex network of proto-oncogenes and tumor-suppressor genes that are components of various signal transduction pathways. Activation of a proto-oncogene(s) and/or a loss of a tumor suppressor gene(s) can lead to the unregulated activity of the cell cycle machinery. This, in turn, will lead to unregulated cell proliferation and to the accumulation of genetic errors which ultimately will result in the development of cancer (Pardee, Science 246:603–608, 1989).

In the eukaryotic cell cycle a key role is played by the cyclin-dependent kinases (CDKs). Cdk complexes are formed via the association of a regulatory cyclin subunit and a catalytic kinase subunit. In mammalian cells, the combination of the kinase subunits (such as cdc2, CDK2, CDK4 or CDK6) with a variety of cyclin subunits (such as cyclin A, B1, B2, D1, D2, D3 or E) results in the assembly of functionally distinct kinase complexes. The coordinated activation of these complexes drives the cells through the cell cycle and ensures the fidelity of the process (Draetta, Trends Biochem. Sci. 15:378–382, 1990; Sherr, Cell 73:1059–1065, 1993). Each step in the cell cycle is regulated by a distinct and specific cyclin-dependent kinase. For example, complexes of Cdk4 and D-type cyclins govern the early G1 phase of the cell cycle, while the activity of the CDK2/cyclin E complex is rate limiting for the G1 to S-phase transition. The CDK2/cyclin A kinase is required for the progression through S-phase and the cdc2/cyclin B complex controls the entry into M-phase (Sherr, Cell 73:1059–1065, 1993).

The CDK complex activity is regulated by mechanisms such as stimulatory or inhibitory phosphorylations as well as the synthesis and degradation of the kinase and cyclin subunit themselves. Recently, a link has been established between the regulation of the activity of cyclin-dependent kinases and cancer by the discovery of a group of CDK inhibitors including the $p27^{Kip1}$, $p21^{Waf1/Cip1}$ and $p16^{Ink4/MTS1}$ proteins. The activity of $p21^{Waf1/Cip1}$ is regulated transcriptionally by DNA damage through the induction of p53, senescence and quiescence (Harper et al., Cell 75:805–816, 1993). The inhibitory activity of $p27^{Kip1}$ is induced by the negative growth factor TGF-β and by contact inhibition (Polyak et al., Cell 78:66–69, 1994). These proteins, when bound to CDK complexes, inhibit their kinase activity, thereby inhibiting progression through the cell cycle. Although their precise mechanism of action is unknown, it is thought that binding of these inhibitors to the CDK/cyclin complex prevents its activation. Alternatively, these inhibitors may interfere with the interaction of the enzyme with its substrates or its cofactors.

While $p21^{Waf1/Cip1}$ and $p27^{Kip1}$ inhibit all the CDK/cyclin complexes tested, $p16^{Ink4/MTS1}$, p15, p18 and p19 block exclusively the activity of the CDK4/cyclin D and CDK6/cyclin D complexes in the early G1 phase (Serrano et al., Nature 366:704–707, 1993), by either preventing the interaction of Cdk4 and Cyclin D1, or indirectly preventing catalysis. As mentioned above, the $p21^{Waf1/Cip1}$ is positively regulated by the tumor suppressor p53 which is mutated in approx. 50% of all human cancers. $p21^{Waf1/Cip1}$ may mediate the tumor suppressor activity of p53 at the level of cyclin-dependent kinase activity. $p16^{Ink4/MTS1}$ is the product of a tumor suppressor gene localized to the 9p21 locus, which is frequently mutated in human cancer cells.

Of all the various kinases, the CDK4/cyclin D complexes are known to play an important role in regulating cell cycle progression in early G1. These complexes function as integrators of various growth factor-induced extracellular signals and as a link between the different signal transduction pathways and other cyclin-dependent kinases. The expression of the cyclin D1 positive regulatory subunit, is deregulated by gene translocations, retroviral insertions and amplifications in parathyroid adenomas, lymphomas, esophageal and breast carcinomas. The targeted overexpression of cyclin D1 in the mammary epithelium of transgenic mice induces mammary adenomas and adenocarcinomas. This confirms that cyclin D1, when overexpressed, acts as an oncogene (Wang et al., Nature 369:669–671, 1994). These data supports the idea that the lack of functional $p16^{Ink4/MTS1}$ or the overexpression of cyclin D1 leads to the deregulation of CDK4/cyclin D1 kinase activity and thereby contribute to uncontrolled cell proliferation.

The prominent role of CDK/cyclin kinase complexes, in particular, CDK4/cyclin D kinase complexes, in the induction of cell proliferation and their deregulation in tumors, makes them ideal targets for developing highly specific anti-proliferative agents.

SUMMARY OF THE INVENTION

In one aspect, the present invention relates to a nucleic acid comprising a nucleotide sequence encoding a chimeric polypeptide having at least two CDK-binding motifs derived from different proteins which bind to cyclin dependent kinases (CDKs). The chimeric polypeptide binds to CDKs and inhibits cell-cycle progression.

The chimeric polypeptide can be a fusion protein, or can be generated by chemically cross-linking the CDK-binding motifs.

In preferred embodiments, at least one of the CDK-binding motifs is a CDK-binding motif of a CDK inhibitor protein, such as an INK4 protein, e.g., p15, p16, p18 and p19, or a CIP protein, e.g., $p21^{CIP1}$, $p27^{KIP1}$, and $p57^{KIP2}$. However, it will be understood that other CDK-binding motifs may be useful. Indeed, the CDK-binding motif of the INK4 proteins is characteristized by tandemly arranged ankyrin-like sequences, which sequences exist in other proteins and, for those which are able to bind a CDK, can be used to generate the subject chimeric proteins. Likewise, the CDK-binding motif can be a p21/p27 inhibitory domain of a protein which has some homology with the CIP protein family. Exemplary chimeric proteins of the present invention are designated by SEQ ID No:2, 5 and 7, and are encoded by the CDS's designated in SEQ ID No:1, 4 and 6.

In preferred embodiments, the CDK-binding motifs of the chimeric protein have different binding specificities, relative to one and other, for cyclin dependent kinases. For instance, the chimeric protein can be generated with a CDK-binding motif from a protein which binds to and inhibits a CDK involved in progression of the cell cycle in $G_0$ and/or $G_1$ phase, and another CDK-binding motif from a protein which binds to and inhibits a CDK involved in progression of the cell cycle in S, $G_2$ and/or M phase. That is, the chimeric protein will bind to and inhibit a plurality (two or more) of cyclin dependent kinases which are active in different phases of the cell-cycle.

In most embodiments, the nucleic acid will further include a transcriptional regulatory sequence for controlling transcription of the nucleotide sequence encoding the chimeric polypeptide, e.g., the transcriptional regulatory sequence is operably linked to a chimeric gene encoding the chimeric polypeptide. For example, the present invention specifically contemplates recombinant transfection systems which include: (i) a gene construct including a nucleic acid encoding a chimeric polypeptide comprising CDK-binding motifs from two or more different proteins which bind to cyclin dependent kinases, and operably linked to a transcriptional regulatory sequence for causing expression of the chimeric polypeptide in eukaryotic cells, and (ii) a gene delivery composition for delivering the gene construct to a cell and causing the cell to be transfected with the gene construct. For example, the gene construct can be derived from a viral vector, such as an adenoviral vector, an adeno-associated viral vector or a retroviral vector. In such embodiments, the gene delivery composition comprises a recombinant viral particle. In other embodiments, the gene construct can be delivered by such means as a liposome or a poly-cationic nucleic acid binding agent. For in vivo delivery to a mammal, such as a human, the gene delivery composition will further include a pharmaceutically acceptable carrier for adminstration to an animal, and, as necessary, will be a sterile preparation and substantially free of pyrogenic agents.

The present invention also pertains to preparations of such chimeric polypeptides. e.g., polypeptides which are generated from CDK-binding motifs from two or more different proteins which bind to cyclin dependent kinases. In preferred embodiments, the chimeric polypeptide is formulated in pharmaceutically acceptable carrier for delivery to a mammal. For example, the chimeric polypeptide can be formulated in liposomal preparations.

Still another aspect of the present invention related to transgenic animals which have cells harboring a nucleic acid one of the subject fusion proteins.

Yet another aspect of the present invention relates to recombinant transfection systems, comprising (i) a first gene construct comprising a coding sequence encoding a inhibitory polypeptide comprising at least one CDK-binding motif for binding and inhibiting activation of a cyclin dependent kinase (cdk), which coding sequence is operably linked to a transcriptional regulatory sequence for causing expression of the first polypeptide in eukaryotic cells, (ii) a second gene construct comprising a coding sequence encoding a endotheliazation polypeptide which promotes endothelialization, and (ii) a gene delivery composition for delivering the gene constructs to a cell and causing the cell to be transfected with the gene construct.

In preferred embodiments, the CDK-binding motif is a CDK-binding motif of a CDK inhibitor protein, such as an INK4 protein (e.g., p15, p16, p18 or p19), or a CIP/KIP protein (e.g., $p21^{CIP1}$, $p27^{KIP1}$, and $p57^{KIP2}$). In other preferred embodiments, the CDK-binding motif comprises tandemly arranged ankyrin-like sequences, or a p21/p27 inhibitory domain.

The inhibitory polypeptide can be a fusion protein comprising CDK-binding motifs from two or more different proteins which bind to cyclin dependent kinases.

In preferred embodiments, the endothelization polypeptide stimulates endothelial cell proliferation and/or stimulates migration of endothelial cells to a wound site. For instance, the endothelization polypeptide is selected from the group consisting of angiogenic basic fibroblast growth factors (bFGF), acid fibroblast growth factor (aFGF), vascular endothelial growth factor (VEGF), platelet derived growth factor (PDGF), vascular permeability growth factor (VPF), and transforming growth factor beta (TGF-β).

In preferred embodiments, the the first and second gene constructs are provided as part of a single vector, and can be provided as part of polycistronic message. Alternatively, the the fisrt and second gene constructs are provided on separate vectors.

In certain embodiments, the gene construct comprises a viral vector, e.g., an adenoviral vector, an adeno-associated viral vector, or a retroviral vector.

In other embodiments, the gene construct is provided in a delivery composition, e.g., selected from the group consisting of a liposome and a poly-cationic nucleic acid binding agent.

The subject transfection systems can be used for treating an animal having a vascular wound characterized a breech of endothelial integrity and by excessive smooth muscle proliferation, by a method which includes administering the recombinant transfection system to the area of the vascular wound. In preferred embodiments, the subject transfection systems are used in the treatment of restenosis, and may be administered by catheter.

Still another aspect of the present invention provides a gene construct encoding a fusion protein comprising a therapeutic polypeptide sequence from an intracellular protein which alter a biological process of a cell upon intracellular localization of the fusion protein, and a transcellular polypeptide sequence for promoting transcytosis of the fusion protein across a cell surface membrane and into a cell.

In preferred embodiments, the trancellular fusion protein alters one or more such biological processes as proliferation, differentiation, cell death, gene expression, protein stability, calcium mobilzation, ion permability, phosphorylation of intracellular proteins, metabolism of inositol phosphates ($IP_3$ and the like, diacyl glycerides, etc), and metabolism of nucleosides (such as cAMP).

The transcellular fusion protein can, by virtue of its binding to a protein or nucleic acid in the targeted cell, alter (inhibit or potentiate) protein-protein interactions or protein-nucleic acid interactions between proteins and nucleic acids endogenous to the cell.

In certain embodiments, the therapeutic polypeptide sequence can be dervied from a tumor suppressor, a transcription factor, a signal transduction protein, an antiviral protein or a metal chelating protein. For instance, the therapeutic polypeptide sequence can include a polypeptide sequence of a tumor supressor such as p53, Rb or an Rb-like protein, or a CKI protein. In other embodiments, the therapeutic polypeptide sequence includes a polypeptide sequence of a signal transduction protein, such as from tubby, a DOT protein, a Bcl protein (bcl-2, bcl-x, etc), or an IκB protein.

In a preferred embodiment, the fusion protein includes at least one CDK-binding motif for binding and inhibiting activation of a cyclin dependent kinase (cdk). For instance, the CDK-binding motif is a CDK-binding motif of a CDK inhibitor protein, such as an INK4 protein (e.g., p15, p16, p18 or p19), or a CIP/KIP protein (e.g., $p21^{CIP1}$, $p27^{KIP1}$, and $p57^{KIP2}$). In other preferred embodiments, the CDK-binding motif comprises tandemly arranged ankyrin-like sequences, or a p21/p27 inhibitory domain. In preferred embodiments, the polypeptide comprises CDK-binding motifs from two or more different proteins which bind to cyclin dependent kinases.

The transcellular polypeptide sequence can be an internalizing peptide, such as may be derived from a polypeptide selected from the group consisting of antepennepedia protein, HIV transactivating (TAT) protein, mastoparan, melittin, bombolittin, delta hemolysin, pardaxin, Pseudomonas exotoxin A, clathrin, Diphtheria toxin and C9 complement protein.

In other embodiments, the transcellular polypeptide sequence can be an accessory peptide sequence which enhances interaction of the fusion protein with a cell surface membrane, such as a peptide sequence that includes an RGD sequence.

In preferred embodiments, the gene construct comprises a viral vector, e.g., an adenoviral vector, an adeno-associated viral vector, or a retroviral vector.

In other embodiments, the gene construct is provided in a delivery composition, e.g., selected from the group consisting of a liposome and a poly-cationic nucleic acid binding agent.

The invention also provides compositions of the fusion protein, e.g., such as may be formulated in pharmaceutical preparations.

The gene construct and the fusion protein may each be used as part of a method for treating an animal for unwanted cell proliferation, by administering the chimeric gene or the fusion protein.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

DETAILED DESCRIPTION OF THE INVENTION

Progression of eukaryotic cells through the cell cycle is governed by the sequential formation, activation, and subsequent inactivation of a series of cyclin/cyclin dependent kinase complexes. The mechanisms underlying the expression of cyclins and the activation of the different cyclin-CDK complexes needed for progression through successive cell cycle transitions are now fairly well understood. In addition to positive regulation by the activation of cyclin-CDK complexes, negative regulation of the cell cycle occurs at checkpoints, many of which operate to control formation of cyclin/CDK complexes and/or activation of the complexes. Accordingly, these transitions are negatively regulated by signals that constrain the cell-cycle until specific conditions are fulfilled. Entry in to mitosis, for example, is inhibited by incompletely replicated DNA or DNA damage. These restriction on cell-cycle progression are essential for preserving the fidelity of the genetic information during cell division. The transition from $G_1$ to S phase, on the other hand, coordinates cell proliferation with environmental cues, after which the checks on the cell-cycle progression tend to be cell autonomous. Disruption of these signaling pathways can uncouple cellular responses from environmental controls and may lead to unrestrained cell proliferation or abherrent loss of differentiation.

(i) Overview

One aspect of the present invention pertains to novel inhibitors of cyclin-dependent kinases (CDKs), particularly CDK/cyclin complexes, which inhibitors can be used to control proliferation and/or differentiation of cells in which the inhibitors are introduced. More specifically, the inhibitors of the invention are chimeric proteins which include CDK-binding motifs from two or more different proteins. Such chimeric proteins are refered to herein as "poly-CBM proteins". For example, as set forth in greater detail below, the subject chimeric proteins can be generated from the in-frame fusion of coding sequences from two different CDK inhibitor proteins (generically refered to herein as "CKI" proteins), such as may be derived from fusion of coding sequences for an INK4 protein and coding sequences for a CIP protein. Moreover, as the appended examples describe, chimeric proteins of the present invention have been observed to be more potent inhibitors of cyclin/CDK complexes than were either of the portions of the chimeric protein individually. For instance, p27-p16 chimeric proteins inhibited a cyclin D1/CDK4 complex with an $IC_{50}$ more than two-fold less than p27 alone, and ten-fold less than p16 alone. Likewise, the p27-p16 chimeric protein inhibited cyclin E/CDK2, cyclin A/CDK2 and cyclin B/CDK2 complexes with $IC_{50}$'s approximately two-fold less than p27 alone (p16 itself not having any significant inhibitory activity against any of the three complexes).

Another aspect of the present invention pertains to chimeric polypeptides, particularly chimeric CKI polypeptides, which includes a heterologous peptide sequence which drives the translocation of an intracellular polypeptide across the cell membrane in order to facilitate localization of the polypeptide in the cellular cytoplasm and/or nucleoplasm to which the polypeptide is ectopically applied. Such chimeric polypeptides are referred to herein as "transcellular polypeptides". In general, such transcellular polypeptides includes a first peptide portion ("internalizing peptide") which by itself is capable of crossing the cellular membrane, e.g., by transcytosis, at a relatively high rate, or which facilitates such transcytosis. The internalizing peptide is conjugated to a polypeptide corresponding to a therapeutic polypeptide, e.g., having intracellular activity, such as the subject CKI polypeptides. The resulting chimeric polypeptide is transported into cells at a much higher rate than the therapeutic polypeptide alone would be, and thereby provide an effective means for introducing the therapeutic polypeptide into cells. The transcellular polypeptide can applied ectopically, or expressed and secreted by cells adjacent to the intended target cells. In the latter embodiment, the internalizing peptide facilitates the uptake of the therapeutic polypeptide by cells proximal to a cell which expresses the recombinant polypeptide. In this manner, the transcellular embodiment of the therapeutic polypeptide can be used to effectively treat cells which are, under the circumstances of treatment, e.g., inefficient or otherwise refractive to transfection with a gene contruct encoding the therapeutic polypeptide. In a preferred embodiment, the transcellular polypeptide is delivered by way of a gene therapy expression vector—e.g., expression of the chimeric polypeptide by a subset of treated cells can result in localization of the polypeptide, with concomitant mitotic inhibition, in neighboring cells. For embodiments of a transcellular CKI polypeptide, the polypeptide can include all or a fragment of a single CKI protein, or include the poly-CBM protein described above.

In still another aspect, the present invention provides methods and compositions for enhancing endothelization of injured sites while concurrently inhibiting smooth muscle cell proliferation around the site. In these embodiments, a CKI polypeptide is co-delivered with a polypeptide (an "endothelization polypeptide") which stimulates (a) endothelial cell proliferation; (b) stimulates migration of endothelial cells to the wound site; (c) inhibits smooth muscle cell migration; and/or (d) inhibits proliferation of smooth muscle cells. In preferred embodiments, the CKI polypeptide and endothelization polypeptide are ultimately delivered in the form of a single expression vector encoding both polypeptides, though multiple transfection of cells with separate expression vectors is also contemplated. The CKI polypeptide can include all or a fragment of a single CKI protein, or can be the poly-CBM protein described above. The co-delivery of the CKI polypeptide and endothelization polypeptide can have beneficial effects in, e.g., the repair of cardiovascular damage, repair of arteriosclerotic lesions and endothelialization of synthetic vascular grafts.

Other aspects of the present invention include: preparations of the subject polypeptides; expression constructs for recombinant production of the subject polypeptides, particularly for use as part of a gene therapy treatment; and methods for modulating cell proliferation and/or differentiation with the subject polypeptides.

(ii) Definitions

For convenience, certain terms employed in the specification, examples, and appended claims are collected here.

The phrase "CDK-binding motif" refers to that portion of a protein which interacts either directly or indirectly with a cyclin dependent kinase (CDK). The binding motif may be a sequential portion of the protein, i.e., a contiguous sequence of amino acids, or it may be conformational, i.e. a combination of non-contiguous sequences of amino acids which, when the protein is in its native folding state, forms a structure which interacts with a CDK. The term "CDK-binding motif" explicitly includes any polypeptide which is identical, substantially homologous, or otherwise functionally or structurally equivalent to a portion of a CKI protein which binds directly or indirectly to a CDK or CDK complex. Other exemplary CDK-binding motifs can be provided from, for example, Rb and Rb-like proteins as well as cyclins.

An "inhibitor of CDK activation" refers to a molecule able to interact with a CDK and prevent activation of a kinase activity of the CDK either by, for example, inhibiting formation of CDK complexes including regulatory subunits, inhibiting interaction of the CDK subunit with activating kinases or phosphatases, inhibiting substrate binding, inhibiting ATP binding, and/or inhibiting conformational changes required for enzymatic activity. Accordingly, such inhibition may be by a direct, competitive mechanism, or by an indirect, non- or uncompetitive mechanism.

As used herein, the term "CKI protein" refers to a protein which can bind to and inhibit activation of a cyclin dependent kinase. Exemplary CKI proteins include members of the INK4 family, such as $p16^{INK4A}$ or $p15^{INK4B}$, and members of the CIP family, such as $p21^{CIP1}$, $p27^{KIP1}$, and $p57^{KIP2}$.

The term "INK4 protein" refers to a family of structurally related CDK inhibitors characterized by a fourfold repeated ankyrin-like sequence (Elledge et al. (1994) Curr. Opin. Cell Biol. 6:874–878), and the ability to bind to CDKs, especially CDK4 and CDK6. Exemplary members of this protein family include p16 (INK4A/MTS1; Serrano et al (1993) Nature 366:704–707); p15 (INK4B; Hannon et al. (1994) Nature 371:257–261); p18 (Guan et al. (1994) Genes Dev. 8:2939–2952) and p19 (Chan et al. (1995) Mol. Cell Biol. 15:2682–2688; and Hirai et al. (1995) Mol. Cell Biol. 15:2672–2681). Other proteins have been identified in the art as having tandemly arranged ankyrin-like sequences, such as the Pho81p protein (Ogawa et al. (1995) Mol. Cell Biol. 15:997–1004), and may provide CDK-binding motifs which are functionally equivalent to those of an INK4 protein.

The term "CIP protein" refers to members of another CKI protein family which includes $p21^{CIP1}$ (WAF1/SDI1/CAP20; Xiong et al. (1993) Nature 366:701–704); $p27^{KIP1}$ (Polyak et al. (1994) Cell 78:67–74); and $p57^{KIP2}$ (Lee et al. (1995) Genes Dev. 9:639–649; and Matsuoka et al. (1995) Genes Dev. 9:650–662). In addition to the functional characteristic of CDK inhibition, the CIP proteins each have a CDK inhibitory motif (a CDK-binding motif) of about 50 amino acids, referred to herein as a "p21/p27" inhibitory domain, which is conserved in members of the CIP family, as well as, for example, members of the Rb-like protein family.

A "chimeric protein" refers to a protein which includes polypeptide sequences from at least two different and distinct proteins. A chimeric protein can be a fusion protein, or the different polypeptide sequences can be covalently linked by a non-peptide bond, e.g., a cross-linking agent.

As used herein, the term "fusion protein" is art recognized and refer to a chimeric protein which is at least initially expressed as single chain protein comprised of amino acid sequences derived from two or more different proteins, e.g., the fusion protein is a gene product of a fusion gene.

The art term "fusion gene" refers to a nucleic acid in which two or more genes are fused resulting in a single open reading frame for coding two or more proteins that as a result of this fusion are joined by one or more peptide bonds.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

As used herein, the term "gene" or "recombinant gene" refers to a nucleic acid comprising an open reading frame encoding a fusion polypeptide of the present invention, including both exonic and (optionally) intronic sequences. An exemplary recombinant gene encoding a subject fusion protein is represented by SEQ ID No:1.

As used herein, the term "transfection" means the introduction of a heterologous nucleic acid, e.g., an expression vector, into a recipient cell by nucleic acid-mediated gene transfer. "Transformation", as used herein with respect to transfected nucleic acid, refers to a process in which a cell's genotype is changed as a result of the cellular uptake of exogenous DNA or RNA, and, for example, the transformed cell expresses a recombinant form of a CDK-inhibitory fusion polypeptide of the present invention.

"Expression vector" refers to a replicable DNA construct used to express DNA which encodes the desired protein and which includes a transcriptional unit comprising an assembly of (1) genetic element(s) having a regulatory role in gene expression, for example, promoters, operators, or enhancers, operatively linked to (2) a DNA sequence encoding a desired protein (in this case, a fusion protein of the present invention) which is transcribed into mRNA and translated into protein, and (3) appropriate transcription and translation initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

In the expression vectors, regulatory elements controlling transcription or translation can be generally derived from mammalian, microbial, viral or insect genes The ability to replicate in a host, usually conferred by an origin of replication, and a selection gene to facilitate recognition of transformants may additionally be incorporated. Vectors derived from viruses, such as retroviruses, adenoviruses, and the like, may be employed.

"Transcriptional regulatory sequence" is a generic term used throughout the specification to refer to DNA sequences, such as initiation signals, enhancers, and promoters and the like which induce or control transcription of protein coding sequences with which they are operably linked. In preferred embodiments, transcription of the fusion gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of one of the naturally-occurring forms of a CDK inhibitor protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g. renal cells, or cells of a neural origin, e.g. neuronal cells. The term also covers so-called "leaky" promoters, which regulate expression of a selected DNA primarily in one tissue, but cause expression in other tissues as well.

"Operably linked" when describing the relationship between two DNA regions simply means that they are functionally related to each other. For example, a promoter or other transcriptional regulatory sequence is operably linked to a coding sequence if it controls the transcription of the coding sequence.

"Recombinant host cells" refers to cells which have been transformed or transfected with vectors constructed using recombinant DNA techniques. As relevant to the present invention, recombinant host cells are those which produce CDK inhibitor fusion proteins by virtue of having been transformed with expression vectors encoding these proteins.

As used herein, a "transgenic animal" is any animal, preferably a non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of a CDK inhibitory fusion protein. The term "chimeric animal" is used herein to refer to animals in which the recombinant gene is found, or in which the recombinant is expressed in some but not all cells of the animal. The term "tissue-specific chimeric animal" indicates that the recombinant gene is present and/or expressed in some tissues but not others.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

(iii) Poly-CBM Polypeptides

One aspect of the invention pertains to chimeric proteins which include CDK-binding motifs from two or more different proteins. In one embodiment, the invention provides a nucleic acid having a nucleotide sequence encoding a chimeric CDK inhibitor protein, and/or equivalents of such nucleic acids. In general, the nucleic acid is derived by the in-frame fusion of coding sequences from two or more proteins which have CDK-inhibitory motifs, such motifs being preserved in the resultant chimeric protein. Accordingly, such chimeric proteins can be derived to include, for example, CKI protein sequences, such as from INK4 or CIP proteins. For instance, as described in the appended examples, a coding sequence providing the CDK-binding motif of an INK4 protein can be fused in frame to a coding sequence providing a CDK-binding motif of a CIP protein.

Exemplary nucleic acid of the present invention encode fusion proteins which include at least a CDK-binding portion of an INK4 protein, such as p15, p16, p18 or p19. In preferred embodiments, the chimeric protein includes at least the two ankyrin-like sequence of the C-terminal portion of the INK4 protein, e.g. corresponding to the $3^{rd}$ request (residues 69–101) and $4^{th}$ repeat (residues 102–133) of $p16^{INK4A}$ (see Serrano et al. (1993) Nature 366:704–707).

Similarly, preferred chimeric proteins of the present invention include at least the p21/27-related inhibitory domain of a CIP protein, e.g. from p21, p27 or p57. For example, the chimeric protein can include the CDK-inhibitory motif corresponding to residues 28–79 of p27, residues 17–68 of p21, and/or residues 31–82 of p57, though larger fragments may be used such as described in the appended examples.

Moreover, CDK-binding motifs homologous to those occurring in either the INK4 or CIP protein families have been observed in other proteins. For example, the p21/p27-related inhibitory domain typical of the CIP protein family has been identified in such other proteins as the Rb-related protein p107 (Zhu et al. (1995) Genes Dev 9:1740–1752). Likewise, ankyrin-like repeats homologous with the INK4 proteins have been identified in such other proteins as the Pho81p protein (Ogawa et al. (1995) Mol Cell Biol 15:997–1004). Consequently, it will be apparent to one of ordinary skill in the art, based on the disclosure herein, that functional equivalents of the INK4 and CIP proteins, e.g. which are capable of binding to a CDK and inhibiting kinase activation, exist and can be provided in the subject chimeric proteins.

Furthermore, it will be understood that the subject chimeric proteins can include CDK-binding motifs from proteins unrelated to either the INK4 family or CIP family. Moreover, such CDK-binding motifs, while inhibitory in and of themselves, can be derived from proteins which are otherwise activating in their full length form. To illustrate, the subject chimeric protein can be generated with a fragment of a cyclin which retains its CDK binding ability but not the CDK activating ability characteristic of the full length protein.

In some instances it may be necessary to introduce an unstructured polypeptide linker region between portions of the chimeric protein derived from different proteins. This linker can facilitate enhanced flexibility of the chimeric protein allowing the CDK-binding motifs from each portion to freely and (optionally) simultaneously interact with a CDK by reducing steric hindrance between the two fragments, as well as allowing appropriate folding of each portion to occur. The linker can be of natural origin, such as a sequence determined to exist in random coil between two domains of a protein. Alternatively, the linker can be of synthetic origin. For instance, the sequence $(Gly_4Ser)_3$ can be used as a synthetic unstructured linker. Linkers of this type are described in Huston et al. (1988) PNAS 85:4879; and U.S. Pat. Nos. 5,091,513 and 5,258,498. Naturally occurring unstructured linkers of human origin are preferred as they reduce the risk of immunogenicity.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a fusion gene sequence (see, for example, Current Protocols in Molecular Biology, eds. Ausubel et al. John Wiley & Sons: 1992).

The term nucleic acid as used herein is intended to include nucleotide sequences encoding functionally equivalent chimeric proteins which, for example, retain the ability to bind to a cyclin-dependent kinase. Equivalent nucleotide sequences will include sequences that differ by one or more nucleotide substitutions, additions or deletions, such as allelic variants; and will, therefore, include sequences that differ from the nucleotide sequence of, for example, an INK4 or CIP gene known in the art due to the degeneracy of the genetic code. Equivalents will also include nucleotide sequences that hybridize under stringent conditions (i.e., equivalent to about 20–27° C. below the melting temperature ($T_m$) of the DNA duplex formed in about 1M salt) to the nucleotide sequence encoding a naturally-occurring CDK-binding motif. Furthermore, equivalent nucleic acids will include those with nucleotide sequences which differ from the natural sequence which encodes a CDK-binding motif because of degeneracy in the genetic code. For example, a number of amino acids are designated by more than one triplet. Codons that specify the same amino acid can, accordingly, be used to replace codons in the naturally-occurring sequence.

This invention also provides expression vectors comprising a nucleotide sequence encoding a subject CDK inhibitor chimeric protein and operably linked to at least one regulatory sequence. Regulatory sequences are art-recognized and are selected to direct expression of the fusion protein. Accordingly, the term regulatory sequence includes promoters, enhancers and other expression control elements. Exemplary regulatory sequences are described in Goeddel; Gene Expression Technology: Methods in Enzymology 185, Academic Press, San Diego, Calif. (1990). For instance, any of a wide variety of expression control sequences-sequences that control the expression of a DNA sequence when operatively linked to it may be used in these vectors to express DNA sequences encoding the fusion proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. Of course, the transcriptional regulatory sequences can include those sequences which naturally control expression of one of the genes used to derive the fusion protein, such as 5' flanking sequences of an INK4 or CIP gene.

It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

Expression vehicles for production of recombinant forms of the subject chimeric proteins include plasmids and other vectors. For instance, suitable vectors for expression of a fusion protein of the present invention include plasmids of the types: pBR322-derived plasmids, pEMBL-derived plasmids, pEX-derived plasmids, pBTac-derived plasmids and pUC-derived plasmids for expression in prokaryotic cells, such as *E. coli.*

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83). These vectors can replicate in *E. coli* due the presence of the pBR322 ori, and in *S. cerevisiae* due to the replication determinant of the yeast 2 micron plasmid. In addition, drug resistance markers such as ampicillin can be used.

The preferred mammalian expression vectors (other than for gene therapy) contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells.

In some instances, it may be desirable to express the subject fusion protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press: 1989) Chapters 16 and 17.

Another aspect of the present invention concerns preparations of the subject chimeric proteins. In particular, purified and semi-purified preparations of the CDK inhibitors can be formulated according to specifications attendant the desired use of the chimeric protein.

With respect to purifying the subject chimeric proteins, Applicant notes that it is widely appreciated that addition of certain heterologous sequences to a protein can facilitate the expression and purification of the proteins. For example, a fusion protein of the present invention can be generated to also include a glutathione-S-transferase (GST) polypeptide sequence. The GST portion of the recombinant proteins can enable easy purification of the protein, such as by the use of glutathione-derivativized matrices (see, for example, Current Protocols in Molecular Biology, eds. Ausabel et al. (N.Y.: John Wiley & Sons, 1991)). In another embodiment, the subject fusion protein can also include a purification leader sequence, such as a poly-(His)/enterokinase cleavage site sequence located at the N-terminus of the subject fusion protein. Such sequences facilitates purification of the poly (His)-expressed fusion protein by affinity chromatography using a $Ni^{2+}$ metal resin. The purification leader sequence can then be subsequently removed by treatment with enterokinase (e.g., see Hochuli et al. (1987) J. Chromatography 411:177; and Janknecht et al. PNAS 88:8972).

The present invention further pertains to methods of producing the subject chimeric proteins. For example, a host cell transfected with a nucleic acid vector directing expression of a nucleotide sequence encoding one of the chimeric proteins of the present invention can be cultured under appropriate conditions to allow expression of the polypeptide to occur. The peptide may be secreted and isolated from a mixture of host cells and medium by inclusion of a signal secretion sequence. Alternatively, the peptide may be retained cytoplasmically and the cells harvested, lysed and the protein isolated. A cell culture includes host cells, media and other byproducts. Suitable media for cell culture are well known in the art. The recombinant chimeric protein can be isolated from cell culture medium, host cells, or both using techniques known in the art for purifying proteins including ion-exchange chromatography, gel filtration chromatography, ultrafiltration, electrophoresis, and immuno-affinity purification with antibodies specific for portions of the chimeric protein.

This invention also pertains to a host cell transfected to recombinantly express one of the subject chimeric proteins. The host cell may be any prokaryotic or eukaryotic cell. Thus, a nucleic acid derived from the fusion of coding sequences for two or more CDK-binding motifs from different proteins can be used to produce a recombinant form of the chimeric protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g., p16, p21, p27, p57, p107, cyclins and the like. Similar procedures, or modifications thereof, can be employed to prepare recombinant chimeric proteins by microbial means or tissue-culture technology in accord with the subject invention.

The chimeric molecules of the present invention can also be generated using well-known cross-linking reagents and protocols. For example, there are a large number of chemical cross-linking agents that are known to those skilled in the art and useful for cross-linking two heterologous polypeptide chains. For the present invention, the preferred cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art. These include: succinimidyl 4-(N-maleimidomethyl)cyclohexane-1-carboxylate (SMCC), m-Maleimidobenzoyl-N-hydroxysuccinimide ester (MBS); N-succinimidyl (4-iodoacetyl)aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyloxycarbonyl- a-methyl-a-(2-pyridyldithio)-tolune (SMPT), N-succinimidyl 3-(2-pyridyldithio) propionate (SPDP), succinimidyl 6-[3-(2-pyridyldithio) propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exists a number of other cross-linking agents including homobifunctional and photoreactive cross-linkers. Disuccinimidyl suberate (DSS), bismaleimidohexane (BMH) and dimethylpimelimidate•2 HCl (DMP) are examples of useful homobifunctional cross-linking agents, and bis-[β-(4-azidosalicylamido)ethyl]disulfide (BASED) and N-succinimidyl-6(4'-azido-2'-nitrophenylamino)hexanoate (SANPAH) are examples of useful photoreactive cross-linkers for use in this invention. For a recent review of protein coupling techniques, see Means et al. (1990) *Bioconjugate Chemistry* 1:2–12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5–7.5) conditions. Halogens (iodoacetyl functions) react with —SH groups at physiological pH's. Both of these reactive groups result in the formation of stable thioether bonds.

The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules. For instance, SMPB has a span of 14.5 angstroms.

Preparing protein-conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

The reaction buffer should be free of extraneous amines and sulfhydryls. The pH of the reaction buffer should be 7.0–7.5. This pH range prevents maleimide groups from reacting with amines, preserving the maleimide group for the second reaction with sulfhydryls.

The NHS-ester containing cross-linkers have limited water solubility. They should be dissolved in a minimal amount of organic solvent (DMF or DMSO) before introducing the cross-linker into the reaction mixture. The cross-linker/solvent forms an emulsion which will allow the reaction to occur.

The sulfo-NHS ester analogs are more water soluble, and can be added directly to the reaction buffer. Buffers of high ionic strength should be avoided, as they have a tendency to "salt out" the sulfo-NHS esters. To avoid loss of reactivity due to hydrolysis, the cross-linker is added to the reaction mixture immediately after dissolving the protein solution.

The reactions can be more efficient in concentrated protein solutions. The more alkaline the pH of the reaction mixture, the faster the rate of reaction. The rate of hydrolysis of the NHS and sulfo-NHS esters will also increase with increasing pH. Higher temperatures will increase the reaction rates for both hydrolysis and acylation.

Once the reaction is completed, the first protein is now activated, with a sulfhydryl reactive moiety. The activated protein may be isolated from the reaction mixture by simple gel filtration or dialysis. To carry out the second step of the cross-linking, the sulfhydryl reaction, the protein chosen for reaction with maleimides, activated halogens, or pyridyl disulfides must contain a free sulfhydryl, usually from a cysteine residue. Free sulfhydryls can be generated by reduction of protein disulfides. Alternatively, a primary amine may be modified with Traut's Reagent to add a sulfhydryl (Blattler et al. (1985) Biochem 24:1517, incorporated by reference herein). Again, Ellman's Reagent can be used to calculate the number of sulfhydryls available in protein.

In all cases, the buffer should be degassed to prevent oxidation of sulfhydryl groups. EDTA may be added to chelate any oxidizing metals that may be present in the buffer. Buffers should be free of any sulfhydryl containing compounds.

Maleimides react specifically with —SH groups at slightly acidic to neutral pH ranges (6.5–7.5). A neutral pH is sufficient for reactions involving halogens and pyridyl disulfides. Under these conditions, maleimides generally react with —SH groups within a matter of minutes. Longer reaction times are required for halogens and pyridyl disulfides.

The first sulfhydryl reactive-protein prepared in the amine reaction step is mixed with the sulfhydryl-containing protein under the appropriate buffer conditions. The protein-protein conjugates can be isolated from the reaction mixture by methods such as gel filtration or by dialysis.

(iv) Transcellular Therapeutic Polypeptides

Another aspect of the present invention pertains to chimeric polypeptides which includes a heterologous peptide sequence ("internalizing peptide") which drives the translocation of an extracellular form of a thereapeutic polypeptide sequence across a cell membrane in order to facilitate intracellular localization of the thereapeutic polypeptide. In this regard, the therapeutic polypeptide sequence is one which is active intracellularly, such as a tumor suppressor polypeptide, transcription factor or the like. The internalizing peptide, by itself, is capable of crossing a cellular membrane by, e.g., transcytosis, at a relatively high rate. The internalizing peptide is conjugated, e.g., as a fusion protein, to a therapeutic polypeptide. The resulting chimeric polypeptide is transported into cells at a higher rate relative to the polypeptide alone to thereby provide an means for enhancing the introduction of inhibitory polypeptides into surrounding cells, e.g., to enhance gene therapy and/or topical applications of the therapeutic polypeptide. For convenience, the transcellular therapeutic polypeptides are described below as fusion proteins including CKI polypeptide sequences, though as also described below (section v), many other protein domains can be used in place of the CKI polypeptide.

In one embodiment, the internalizing peptide is derived from the drosopholia antepennepedia protein, or homologs thereof. The 60 amino acid long long homeodomain of the homeo-protein antepennepedia has been demonstrated to translocate through biological membranes and can facilitate the translocation of heterologous polypeptides to which it is couples. See for example Derossi et al. (1994) *J Biol Chem* 269:10444–10450; and Perez et al. (1992) *J Cell Sci*

102:717–722. Recently, it has been demonstrated that fragments as small as 16 amino acids long of this protein are sufficient to drive internalization. See Derossi et al. (1996) *J Biol Chem* 271:18188–18193. The present invention contemplates a chimeric protein comprising at least one CDK binding motif and at least a portion of the antepennepedia protein (or homolog thereof) sufficient to increase the transmembrane transport of the chimeric protein, relative to the CDK binding motif alone, by a statistically significant amount.

Another example of an internalizing peptide is the HIV transactivator (TAT) protein. This protein appears to be divided into four domains (Kuppuswamy et al. (1989) *Nucl. Acids Res.* 17:3551–3561). Purified TAT protein is taken up by cells in tissue culture (Frankel and Pabo, (1989) *Cell* 55:1189–1193), and peptides, such as the fragment corresponding to residues 37–62 of TAT, are rapidly taken up by cell in vitro (Green and Loewenstein, (1989) *Cell* 55:1179–1188). The highly basic region mediates internalization and targeting of the internalizing moiety to the nucleus (Ruben et al., (1989) *J. Virol.* 63:1–8). Peptides or analogs that include a sequence present in the highly basic region, such as CFITKALGISYGRKKRRQRRRPPQGS (SEQ ID No:29), are conjugated to CKI polypeptides (or CDK binding motifs thereof) to aid in internalization and targeting those proteins to the intracellular milleau.

Another exemplary transcellular CKI polypeptide can be generated to include a sufficient portion of mastoparan (T. Higashijima et al., (1990) *J. Biol. Chem.* 265:14176) to increase the transmembrane transport of the chimeric protein.

While not wishing to be bound by any particular theory, it is noted that hydrophilic polypeptides may be also be physiologically transported across the membrane barriers by coupling or conjugating the polypeptide to a transportable peptide which is capable of crossing the membrane by receptor-mediated transcytosis. Suitable internalizing peptides of this type can be generated using all or a portion of, e.g., a histone, insulin, transferrin, basic albumin, prolactin and insulin-like growth factor I (IGF-I), insulin-like growth factor II (IGF-II) or other growth factors. For instance, it has been found that an insulin fragment, showing affinity for the insulin receptor on capillary cells, and being less effective than insulin in blood sugar reduction, is capable of transmembrane transport by receptor-mediated transcytosis and can therefor serve as an internalizing peptide for the subject transcellular CKI polypeptides. Preferred growth factor-derived internalizing peptides include EGF (epidermal growth factor)-derived peptides, such as CMHIESLDSYTC (SEQ ID No:30) and CMYIEALDKYAC (SEQ ID No:31); TGF-beta (transforming growth factor beta)-derived peptides; peptides derived from PDGF (platelet-derived growth factor) or PDGF-2; peptides derived from IGF-I (insulin-like growth factor) or IGF-II; and FGF (fibroblast growth factor)-derived peptides.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0–5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of CKI polypeptides, taken up by an endocytic mechanism, from endosomal compartments to the cytoplasm.

A preferred pH-dependent membrane-binding internalizing peptide includes a high percentage of helix-forming residues, such as glutamate, methionine, alanine and leucine. In addition, a preferred internalizing peptide sequence includes ionizable residues having pKa's within the range of pH 5–7, so that a sufficient uncharged membrane-binding domain will be present within the peptide at pH 5 to allow insertion into the target cell membrane.

A particularly preferred pH-dependent membrane-binding internalizing peptide in this regard is aa1-aa2-aa3-EAALA(EALA)4-EALEALAA-amide (SEQ ID No:32), which represents a modification of the peptide sequence of Subbarao et al. (*Biochemistry* 26:2964, 1987). Within this peptide sequence, the first amino acid residue (aa1) is preferably a unique residue, such as cysteine or lysine, that facilitates chemical conjugation of the internalizing peptide to a targeting protein conjugate. Amino acid residues 2–3 may be selected to modulate the affinity of the internalizing peptide for different membranes. For instance, if both residues 2 and 3 are lys or arg, the internalizing peptide will have the capacity to bind to membranes or patches of lipids having a negative surface charge. If residues 2–3 are neutral amino acids, the internalizing peptide will insert into neutral membranes.

Yet other preferred internalizing peptides include peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked CKI polypeptide into the cell cytoplasm. Such internalizing peptides may be modeled after sequences identified in, e.g., Pseudomonas exotoxin A, clathrin, or Diphtheria toxin.

Pore-forming proteins or peptides may also serve as internalizing peptides herein. Pore forming proteins or peptides may be obtained or derived from, for example, C9 complement protein, cytolytic T-cell molecules or NK-cell molecules. These moieties are capable of forming ring-like structures in membranes, thereby allowing transport of attached CKI polypeptide through the membrane and into the cell interior.

Mere membrane intercalation of an internalizing peptide may be sufficient for translocation of the CKI polypeptide across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyl transferase, such as GNAAAARR (SEQ ID NO:33) (Eubanks et al., in Peptides. Chemistry and Biology, Garland Marshall (ed.), ESCOM, Leiden, 1988, pp. 566–69). In this construct, an internalizing, peptide would be attached to the C-terminus of the accessory peptide, since the N-terminal glycine is critical for the accessory moiety's activity. This hybrid peptide, upon attachment to a CKI polypeptide at its C-terminus, is N-myristylated and further anchored to the target cell membrane, e.g., it serves to increase the local concentration of the CKI polypeptide at the cell membrane.

To further illustrate use of an accessory peptide, a phosphorylatable accessory peptide is first covalently attached to the C-terminus of an internalizing peptide and then incorporated into a fusion protein with a CKI polypeptide. The peptide component of the fusion protein intercalates into the target cell plasma membrane and, as a result, the accessory peptide is translocated across the membrane and protrudes into the cytoplasm of the target cell. On the cytoplasmic side of the plasma membrane, the accessory peptide is phosphorylated by cellular kinases at neutral pH. Once phosphorylated, the accessory peptide acts to irreversibly anchor the fusion protein into the membrane. Localization to the cell surface membrane can enhance the translocation of the CKI polypeptide into the cell cytoplasm.

Suitable accessory peptides include peptides that are kinase substrates, peptides that possess a single positive charge, and peptides that contain sequences which are glycosylated by membrane-bound glycotransferases. Accessory peptides that are glycosylated by membrane-bound glycotransferases may include the sequence x-NLT-x, where "x" may be another peptide, an amino acid, coupling agent or hydrophobic molecule, for example. When this hydrophobic tripeptide is incubated with microsomal vesicles, it crosses vesicular membranes, is glycosylated on the luminal side, and is entrapped within the vesicles due to its hydrophilicity (C. Hirschberg et al., (1987) *Ann. Rev. Biochem.* 56:63–87). Accessory peptides that contain the sequence x-NLT-x thus will enhance target cell retention of corresponding CKI polypeptide.

In another embodiment of this aspect of the invention, an accessory peptide can be used to enhance interaction of the CKI polypeptide with the target cell. Exemplary accessory peptides in this regard include peptides derived from cell adhesion proteins containing the sequence "RGD", or peptides derived from laminin containing the sequence CDPGYIGSRC (SEQ ID No:34). Extracellular matrix glycoproteins, such as fibronectin and laminin, bind to cell surfaces through receptor-mediated processes. A tripeptide sequence, RGD, has been identified as necessary for binding to cell surface receptors. This sequence is present in fibronectin, vitronectin, C3bi of complement, von-Willebrand factor, EGF receptor, transforming growth factor beta, collagen type I, lambda receptor of *E. coli*, fibrinogen and Sindbis coat protein (E. Ruoslahti, Ann. Rev. Biochem. 57:375–413, 1988). Cell surface receptors that recognize RGD sequences have been grouped into a superfamily of related proteins designated "integrins". Binding of "RGD peptides" to cell surface integrins will promote cell-surface retention, and ultimately translocation, of the CKI fusion protein.

As described for the poly-CBM proteins above, the internalizing and accessory peptides can each, independently, be added to a CKI polypeptide by either chemical cross-linking or in the form of a fusion protein. In the instance of fusion proteins, unstructured polypeptide linkers can be included between each of the peptide moieties.

The CKI polypeptide can consist of as little as a CDK-binding moitey of a CKI protein, or can include a full length CKI protein and/or poly-CBM protein.

In general, the internalization peptide will be sufficient to also direct export of the CKI polypeptide. However, where an accessory peptide is provided, such as an RGD sequence, it may be necessary to include a secretion signal sequence to direct export of the fusion protein from its host cell. In preferred embodiments, the secretion signal sequence is located at the extreme N-terminus, and is (optionally) flanked by a proteolytic site between the secretion signal and the rest of the fusion protein.

In an exemplary embodiment, the CKI polypeptides is engineered to include an integrin-binding RGD peptide/SV40 nuclear localization signal (see, for example Hart S L et al., 1994; J. Biol. Chem.,269:12468–12474), such as encoded by the nucleotide sequence provided in the Nde1-EcoR1 fragment: catatgggtggctgccgtggcgatatgt-tcggttgcggtgctcctccaaaaaagaagagaaaggtagctggattc (SEQ ID No:9), which encodes the RGD/SV40 nucleotide sequence: MGGCRGDMFGCGAPPKKKRKVAGF (SEQ ID No:10). In another embodiment, the protein can be engineered with the HIV-1 tat(1–72) polypeptide, e.g., as provided by the Nde1-EcoR1 fragment:catatggagccagtagatcctagactagagccctggaagcatccaggaagtcagcctaaaactgcttgtaccaattgctattgtaaaaagtgttgctttcattgccaagtttgtttcataacaaaagcccttggcatctcctatggcaggaagaagcggagacagcgacgaagacctcctcaaggcagtcagactcatcaagtttctctaagtaagcaaggattc (SEQ ID No:11), which encodes the HIV-1 tat(1–72) peptide sequence: MEPVD-PRLEPWKHPGSQPKTACTNCYCKKCCFH-CQVCFITKALGISYGRKKRRQRRR PPQGSQTHQVSL-SKQ (SEQ ID No:12). In still another embodiment, the fusion protein includes the HSV-1 VP22 polypeptide (Elliott G., O'Hare P (1997) *Cell,* 88:223–233) provided by the Nde1-EcoR1 fragment:

```
                                                                  (SEQ ID NO:13)
cat atg acc tct cgc cgc tcc gtg aag tcg ggt ccg cgg gag gtt ccg cgc gat gag tac gag gat ctg tac tac

acc ccg tct tca ggt atg gcg agt ccc gat agt ccg cct gac acc tcc cgc cgt ggc gcc cta cag aca cgc tcg

cgc cag agg ggc gag gtc cgt ttc gtc cag tac gac gag tcg gat tat gcc ctc tac ggg ggc tcg tca tcc gaa

gac gac gaa cac ccg gag gtc ccc cgg acg cgg cgt ccc gtt tcc ggg gcg gtt ttg tcc ggc ccg ggg cct gcg

cgg gcg cct ccg cca ccc gct ggg tcc gga ggg gcc gga cgc aca ccc acc acc gcc ccc cgg gcc ccc cga

acc cag cgg gtg gcg act aag gcc ccc gcg gcc ccg gcg gcg gag acc acc cgc ggc agg aaa tcg gcc cag
```

-continued cca gaa tcc gcc gca ctc cca gac gcc ccc gcg tcg acg gcg cca acc cga tcc aag aca ccc gcg cag ggg ctg gcc aga aag ctg cac ttt agc acc gcc ccc cca aac ccc gac gcg cca tgg acc ccc cgg gtg gcc ggc ttt aac aag cgc gtc ttc tgc gcc gcg gtc ggg cgc ctg gcg gcc atg cat gcc cgg atg gcg gcg gtc cag ctc tgg gac atg tcg cgt ccg cgc aca gac gaa gac ctc aac gaa ctc ctt ggc atc acc acc atc cgc gtg acg gtc tgc gag ggc aaa aac ctg ctt cag cgc gcc aac gag ttg gtg aat cca gac gtg gtg cag gac gtc gac gcg gcc acg gcg act cga ggg cgt tct gcg gcg tcg cgc ccc acc gag cga cct cga gcc cca gcc cgc tcc gct tct cgc ccc aga cgg ccc gtc gag gaa ttc which encodes the HSV-1 VP22 peptide having the sequence:

(SEQ ID NO:14)

MTSRRSVKSGPREVPRDEYEDLYYTPSSGMASPDSPPDTSRRGALQTRSRQRGEVRFVQ

YDESDYALYGGSSSEDDEHPEVPRTRRPVSGAVLSGPGPARAPPPPAGSGGAGRTPTTAP

RAPRTGRVATKAPAAPAAETTRGRKSAQPESAALPDAPASTAPTRSKTPAQGLARKLHF

STAPPNPDAPWTPRVAGFNKRVFCAAVGRLAAMHARMAAVQLWDMSRPRTDEDLNE

LLGITTIRVTVCEGKNLLQRANELVNPDVVQDVDAATATRGRSAASRPTERPRAPARSA

SRPRRPVE

In still another embodiment, the fusion protein includes the C-terminal domain of the VP22 protein from, e.g., the nucleotide sequence (Nde1-EcoR1 fragment):

(SEQ ID NO:15)

cat atg gac gtc gac gcg gcc acg gcg act cga ggg cgt tct gcg gcg tcg cgc ccc acc gag cga cct cga gcc cca gcc cgc tcc gct tct cgc ccc aga cgg ccc gtc gag gaa ttc which encodes the VP22 (C-terminal domain) peptide sequence:

(SEQ ID NO:16)

MDVDAATATRGRSAASRPTERPRAPARSASRPRRPVE (v) Transcellular Polypeptides as General Gene Therapy Agents Another aspect of the present invention pertains generally to the use of internalizing peptides as part of a strategy to deliver therapeutic proteins by gene therapy techniques. In addition to the subject CKI polypeptides, other therapeutic proteins such as various tumor suppressors, transcription factors, signal transduction proteins, antiviral polpeptides, and therapeutic peptides, e.g., which are otherwise localized intracellularly, can be engineered to include an internalizing peptide which drives the translocation of the therapeutic polypeptide into surrounding cells. Thus, the transcytosis system can be used to increase the efficacy of gene therapy by delivering the therapeutic protein not only to cells actually transfected with the expression vector, but also to the surrounding cells. Such constructs can be generated with other therapeutic polypeptides using such of the general teachings herein as applicable and the general knowledge in the art.

In one illustrative embodiment, the therapeutic polypeptide sequence is derived from a tumor suppressor. In addition to the CKI proteins described above, exemplary tumor suppressors from which the subject transcellular proteins can be generated include the Rb protein (and related proteins) and the p53 protein. For instance, the subject constructs can be generated with a therapeutic polypeptide domain comprising at least a functional domain of Rb, p107 or other Rb-like protein. Such tumor suppressor domains have been mapped through both genetic and biochemical means. (Hu et al. (1990) *EMBO J.* 9:1147–1155; Ewen et al. (1991) *Cell* 66:1155–1164; Ewen et al. (1992) *Science* 255:85–87). An approximately 400 amino acid fragment of Rb and p107, termed the Rb pocket, is responsible for association of these proteins with the DNA tumor virus oncoproteins and cellular ligands. Within this domain are six regions of extensive sequence similarity between Rb and p107. (Ewen et al. (1991), supra).

Another class of tumor suppressors which can be used to generate the subject transcellular proteins include the DOTs (also dpc-4 and MAD-like proteins in the literature). Exemplary members of the this protein family include GenBank accession numbers U76622, U59913, U59911, U68019, U65019, U68018, U68019, 1438077, U59913 and U59912. These proteins are involved in intracellular signal transduction events downstream of TGFβ (superfamily) receptors. For instance, it has been previously shown that Smad3 and Smad4 (the product of the tumor suppressor gene DPC-4) strongly synergize to induce strong ligand-independent TGF-β-like responses, and that inactive carboxy-terminally truncated mutants of either Smad act as dominant-negative inhibitors of the natural TGF-beta response. Zhang et al. (1997) *Curr Biol* 7:270–276. DPC-4 has been reported as a candidate tumour suppressor. Thus, agonist and antagonist (dominant negative) forms of the DOT proteins can be used to generate trancellular polypeptides which alter the response of a cell to TGFβ's.

Another illustrative example of the subject transcellular proteins include fusion proteins generated with Bcl-2 or Bcl-x polypeptide sequences. The protein Bcl-2 plays a central role in the process of programmed cell death by blocking apoptosis. For example, when Bcl-2 levels in a cell are elevated, apoptosis is blocked. Conversely, when Bcl-2 levels in a cell are lowered, the rate of cell death is accelerated. The protein encoded by the bcl-2 proto-oncogene has been reported to be capable of inhibiting apoptosis in many hematopoietic cell systems. The bcl-2 protein is a 26 kD membrane-associated cytoplasmic protein (Tsujimoto et al. (1987) *Oncogene* 2: 3; U.S. Ser. No. 5,202,429 and U.S. Ser. No. 5,015,568; Hockenbery et al. (1991) *PNAS* 88:6961; Monaghan et al. (1992) *J. Histochem. Cytochem.* 40:1819; Nguyen et al. (1993) *J Biol. Chem.* 268: 25265; and Nguyen et al. (1994) *J. Biol. Chem.* 269:16521). The capacity of bcl-2 to enhance cell survival is related to its ability to inhibit apoptosis initiated by several factors, such as cytokine deprivation, radiation exposure, glucocorticoid treatment, and administration of anti-CD-3 antibody. Thus, all or a portion of bcl-2 sufficient to inhibit apoptosis can be used to generate the subject transcellular proteins.

Likewise, the transcellular protein can be generated using all or a portion of a protein which interacts with and/or is structurally related to the bcl-2 gene product have also been identified, such as for example bcl-$x^L$ and bcl-$x^S$ [Boise et al. (1993) *Cell* 74: 597; Gonzalez-Garcia et al. (1994) *Development* 120: 3033; Gottschalk et al. (1994) *PNAS* 91: 7350], Bax [Oltvai et al. (1993) *Cell* 74: 609], Mcl-1 [Kozopas et al. (1993) *PNAS* 90: 3516], and A1 [Lin et al. (1993) *J. Immunol.* 151: 179].

An example of a signal transduction protein which can be used to generate the subject transcellular proteins is the product the mammalian tubby (tub) genes, e.g., which are involved in the control of mammalian body weight. See, for example, U.S. Ser. No. 5,646,040. Tubby, an autosomal recessive mutation recently found to be the result of a splicing defect in the tubby gene. Thus, agonist and antagonist forms of tubby proteins can be used to control weight gain in animals. Moreover, these proteins are also excellent candidates for use in the treatment of ocular diseases as mutations in the tubby gene are known to lead to early progressive retinal degeneration.

Still another family of proteins which can be used to generate a transcellular protein of the present invention are the IκB proteins. The nuclear factor-κB (NF-κB) is an inducible transcription factor which participates in the regulation of multiple cellular genes after treatment of cells with a variety of factors. These genes are involved in the immediate early processes of immune, acute phase, and inflammatory responses. NF-κB has also been implicated in the transcriptional activation of several viruses, most notably the type 1 human immunodeficiency virus (HIV-1) and cytomegalovirus (CMV) (Nabel et al. (1987) *Nature* 326:711; Kaufman et al. (1987) *Mol. Cell. Biol.* 7:3759; and Sambucetti et al. (1989) *EMBO J* 8:4251).

Activation of the NF-κB transcription factor and various related forms can be initiated by a variety of agents, including TNF-α, phorbol 12-myristate 13-acetate (PMA), interleukin-1 (IL-1) and interleukin-2 (IL-2). Activation proceeds through a post-translational event in which preformed cytoplasmic NF-κB in the Rel complex is released from a cytoplasmic inhibitory protein. A common feature of the regulation of transcription factors which belong to the Rel-family is their sequestration in the cytoplasm as inactive complexes with a class of inhibitory molecules known as IκBs (Baeuerle et al. (1988) *Cell* 53:211; Beg et al. (1993) *Genes Dev.* 7:2064; and Gilmore et al. (1993) *Trends in Genetics* 9:427). Treatment of cells with different inducers, e.g., IL-1, TNF-α, LPS, dsRNA or PMA, results in dissociation of the cytoplasmic complexes and translocation of free NF-κB to the nucleus (Grilli et al. (1993) *International Rev. of Cytology* 143:1–62; Baeuerle et al. (1994) *Annu. Rev. Immunol.* 12:141). The dissociation of the cytoplasmic complexes is understood to be triggered by the phosphorylation and subsequent degradation of the IκB protein (Palombella et al. (1994) *Cell* 78:773; Ghosh et al. (1990) *Nature* 344:678).

Thus, the IκB proteins provide a therapeutic target for being upregulated, such as be ectopic expression through gene therapy. Accordingly, the subject transcellular protein can be generated with an IκB polypeptide sufficient to bind to and prevent nuclear localization of NF-κB. In preferred embodiments, the IκB polypeptide has been altered, e.g., by point mutagenesis or truncation, to increase the intracellular half-life of the fusion protein. For instance, Lys-25 and Lys-26 of human IκBα can be mutated to remove the ability of the protein to be ubiquitinated.

In still other embodiments, the trancellular protein can be generated with a transcription factor polypeptide, as well as with a transcription repressor polypeptide, e.g., to potentiate or inhibit the expression of a gene. In other embodiments, the therapeutic portion of the trancellular protein can be provided from a metal binding protein, e.g., for use in inhibiting the action of intracellular DNA damaging agents such as cisplatin.

In yet other embodiments, the therapeutic polypeptide of the trancellular fusion protein can be derived from small peptides/polypeptides which are artificial in sequence, or which are truncated forms of any of such proteins as described above. In an illustrative embodiment, the therapeutic polypeptide can be a peptide inhibitor of cyclin dependent kinases, such described in U.S. Ser. Pat. No. 5,625,031.

In general, the criteria for selecting the therapeutic polypeptide portion of the transcellular protein is reasonably straightforward. As with the CKI polypeptides, the therapeutic polypeptide sequence included in the fusion protein should from an intracellular protein which modulates a biological process in the cell, e.g., by either mimicing or antagonizing the wild-type form of the protein from which it is derived. The therapeutic polypeptide sequence included in the fusion protein preferably does not includes any membrane association sequences, such as transmembrane domains, myristolation sequences, etc. The therapeutic polypeptide sequence also preferably does not includes any disulfide bonds. It is preferably no larger than about 100 kD, and is even more preferably no larger than 75, 50 or even 30 kd. It is also preferably no smaller than about 20 amino acids residues.

(vi) Co-delivery of CKI Polypeptides and Endothelialization Polypeptides

CKI polypeptides, including those chimeric CKI polypeptides described above, can be used to inhibit proliferation of smooth muscle cells, and can therefore be used as part of a therapeutic regimen in the treatment of a patient suffering from a condition which is characterized by excessive smooth muscle proliferation.

The arterial wall is a complex multicellular structure and is important in the regulation of inflammation, coagulation, and regional blood flow. Vascular smooth muscle cells (SMCs) are located predominantely in the arterial tunica media and are important regulators of vascular tone and blood pressure. These cells are normally maintained in a nonproliferative state in vivo. Arterial injury results in the migration of SMCs into the intimallayer of the arterial wall, where they proliferate and synthesize extracellular matrix components.

Arterial intimal thickening after injury is the result of the following series of events: 1) initiation of smooth muscle cell proliferation within hours of injury, 2) SMC migration to the intima, and 3) further SMC proliferation in the intima with deposition of matrix. Investigations of the pathogenesis of intimal thickening following arterial injury have shown that platelets, endothelial cells, macrophages and smooth muscle cells release paracrine and autocrine growth factors (such as platelet derived growth factor, PDGFα), epidermal growth factor, insulin-like growth factor, and transforming growth factor and cytokines that result in the smooth muscle cell proliferation and migration. T-cells and macrophages also migrate into the neotima. This cascade of events is not limited to arterial injury, but also occurs following injury to veins and arterioles. The overall disease process can be termed a hyperproliferative vascular disease because of the etiology of the disease process.

Vascular injury causing intimal thickening can be broadly categorized as being either biologically or mechanically induced. One of the most commonly occurring forms of biologically mediated vascular injury leading to stenosis is Atherosclerosis. The migration and proliferation of vascular smooth muscle plays a crucial role in the pathogenesis of atherosclerosis. Atherosclerotic lesions include massive accumulation of lipid laden "foam cells" derived from monocyte/macrophage and smooth muscle cells. Formation of "foam cell" regions is associated with a breech of endothelial integrity and basal lamina destruction. Triggered by these events, restenosis is produced by a rapid and selective proliferation of vascular smooth muscle cells with increased new basal lamina (extracellular matrix) formation and results in eventual blocking of arterial pathways (Davies).

Mechanical injuries leading to intimal thickening result following balloon angioplasty, vascular surgery, transplantation surgery, and other similar invasive processes that disrupt vascular integrity. Although balloon angioplasty can dilate arterial stenosis effectively, restenosis occurs in 30–40% of patients after 6 months. Intimal thickening following balloon catheter injury has been studied in animals as a model for arterial restenosis that occurs in human patients following balloon angioplasty. De-endothelialization with an intraarterial catheter, which dilates an artery, injures the innermost layers of medial smooth muscle and may even kill some of the innermost cells.

Injury to the innermost layers of medial smooth muscle is followed by a proliferation of the medial smooth muscle cells, after which many of them migrate into the intima through fenestrae in the internal elastic lamina and proliferate to form a neointimal lesion.

Smooth muscle cell proliferation is a critical event in the pathogenesis of atherosclerosis and transplant arteriosclerosis as well as in the response to injury arising from all forms of vascular reconstruction such as angioplasty (Raines et al. (1993) *Br. Heart J.* 69 (Supplement), S 30; Clowes et al. (1991) *Vasc. Surg* 13:885; and Isik et al. (1992) *Am. J. Pathol.* 141:1139). Invasive cardiovascular surgical procedures, such as percutaneous translumenal coronary angioplasty (PTCA, using a balloon catheter) and aorto-coronary bypass surgery (ACBS), that are currently employed in treating the coronary stenosis or occlusion caused by atherosclerosis represent a major therapeutic advance for managing coronary heart disease (CHD). However, the cellular proliferative response and associated intimal hyperplasia that can follow the damage to blood vessels that occurs with these procedures leads to complications which cannot be effectively controlled by presently available drugs, and can be more detrimental than the original condition. The development of these complications, termed restenosis (in the case of PTCA) or stenosis (in the case of ACBS), has similarities to the development of atherosclerosis.

However, reendothelialization of the injured area concurrent with smooth muscle cell proliferation is a major consideration for inhibiting restenosis (Casscells, W. Circulation 1992, 86, 722; Reidy, M. A.; Lidner, V. in endothelial Cell Dysfunctions, Simionescu, N. and Simionescu M., Ed. Plenum Press, NY N.Y., (1992), 31). Thus, any successful approach to inhibiting SMC proliferation should not interfere with endothelial cell repair or the normal function of other cell types (Weissberg, P. L.; Grainger, D. J.; Shanahan C. M.; Metcalfe, J. C. Cardiovascular Res. 1993, 27, 1191).

Accordingly, the present invention provides compositions and methods for treating patients suffering from disorders marked by unwanted proliferation of smooth muscle cells where endothelization is a desired goal in addition to inhibiting proliferation of SMCs. In one aspect, the method of the present invention arranges for simultaneous delivery of a CKI polypeptide along with a second polypeptide (an "endothelization polypeptide") which (a) stimulates endothelial cell proliferation; (b) stimulates migration of endothelial cells to the wound site; and/or (c) inhibits smooth muscle cell migration. For instance, in an attempt to prevent restenosis or reduced intimal smooth muscle cell proliferation following angioplasty, the present compositions can be employed clinically, concurrent with or following angioplasty.

Exemplary endothelization polypeptides which can be do-delivered with a CKI polypeptide include angiogenic basic fibroblast growth factors (bFGF), acid fibroblast growth factor (aFGF), vascular endothelial growth factor (VEGF), platelet derived growth factor (PDGF), vascular permeability growth factor (VPF), transforming growth factor beta (TGF-β) and various cytokines. Related molecules which operate in a similar fashion may also be used. Other endothelization polypeptides include those which may stimulate re-endothelial growth by, e.g., stimulating VEGF production by vascular smooth muscle cells, or inhibit smooth muscle cell migration by, e.g., down-regulating or antagonizing vascular smooth muscle cell PDGF receptors.

In a preferred embodiment, the endothelization polypeptide is derived from basic FGF, such as a human bFGF. Basic FGF is an effective mitogen for vascular smooth muscle cells in the medial layer of the artery wall. For instance, a human bFGF molecule that was purified from placenta ("placental bFGF") was shown to (a) stimulate capillary endothelial cell proliferation, (b) to stimulate chemotaxis in capillary endothelial cells and (c) to stimulate these same cells to produce plasminogen activator and latent collagenase.

Another exemplary polypeptide that can be co-delivered with the subject CKIs is acidic fibroblast growth factor (aFGF). It has been demonstrated that intravenous administration of aFGF promotes vascular repair in the rat carotid artery model of restenosis, and therefore may be efficacious in the prevention of restenosis (Bjornsson et al., (1991) *PNAS* 88: 8651–8655).

In yet another preferred embodiment, the endothelialization polypeptide is derived from a vascular endothelial growth factor, particular a human VEGF.

As is clear from the context above, also included within the scope of the term "endothelialization polypeptide" are biologically active fragments thereof, as well as N-terminally or C-terminally extended versions thereof or analogs thereof substituting and/or deleting or inserting one or more amino acid residues which retain qualitatively the biological activities of the protein described herein. For instance, preferred homologs include those in which one or more cysteine residues not required for biological activity are substituted by a different amino acid residue, preferably serine. Substitution of one or more cysteine residues reduces the opportunity for intermolecular and intramolecular disulfide bond formation, thereby rendering the molecule more stable. There are nine cysteine residues that are present in human VEGF121, bovine VEGF120, human VEGF165 and bovine VEGF164. Of these, eight are conserved with PDGF. Accordingly, the most preferred analog is one in which the ninth cysteine residue is substituted by serine. This cysteine residue is present at position 160 of hVEGF165 and position 116 of hVEGF121 and the corresponding positions in the bovine forms. Amino acid substitutions can be accomplished by site specific mutagenesis of the DNA sequences described herein using well known techniques (see, e.g., Zoller, M. J. and Smith, M., Nucleic Acids Research (1982) 10:6487–6500).

While the native form of the bovine vascular endothelial cell growth factor is apparently glycosylated, there is currently no evidence that glycosylation is essential for biological activity. Accordingly, biologically active non-glycosylated or partially glycosylated forms, which can be produced by prokaryotic host cells or by mutation of glycosylation sites in the protei, are included within the scope of VEGF and the other endothelialization polypeptides.

In another embodiment, the endothelialization polypeptide comprises an epidermal growth factor (EGF) polypeptide coupled with hyaluronic acid (HA). HA/EGF formulations have been demonstrated to stimulate reendothelialization in the anterior chamber of the eye. Hyaluronic acid (HA) is one of the mucopolysaccharides having a straight chain structure consisting of the repetition of a disaccharide unit of N-acetylglucosamine and glucuronic acid. HA is found in nature, in microorganisms and in the skin and connective tissue of humans and other animals.

Moreover, the glycosaminoglycans (GAGs) heparin and heparan sulfate (HS) are endogenous inhibitors of SMC proliferation, yet are able to promote endothelial cell growth (Castellot (1987) *Seminars in Thrombosis and Hemostasis* 13:489; and Wight, T. N. (1989) *Arteriosclerosis* 9:1). The endothelization polypeptide can be derived from a protein which naturally includes HS GAG chains, or which has been engineered to artificially include HS GAG chains. See, for example, U.S. Pat. No. 5,486,599.

There are a variety of assays available for rapidly accessing the suitability of a potential endothelialization polypeptide. For instance, mitogenic activity for vascular endothelial cells can be determined by an assay which uses, as target cells, adrenal cortex-derived capillary endothelial cells (ACE cells). This assay is carried out essentially as described in Gospodarowicz et al., (1986) *J Cell Physiol.* 127:121–136). Generally, stock cultures of ACE cells are maintained in the presence of Dulbecco's modified Eagle's medium (DMEM-21) supplemented with 10% calf serum. The antibiotics penicillin (50 IU/ml), streptomycin (50 mu g/ml), gentamycin (50 mu g/ml), and Fungizone (0.25 mu g/ml) and 2 mM L-glutamine can also be added to the medium. Cells are passaged weekly on tissue culture dishes at a split ratio of between 1:40 and 1:200 (the preferred split ratio is that which gives $2.5\times10^5$ cells in 15 ml of medium in T75 flasks). For the mitogenic assay, cells are seeded in 12 well cluster plates at a density of $5\times10^3$ cells per well in 1 ml Dulbecco's modified Eagle's medium supplemented with 10% calf serum and antibiotics as described in Gospodarowicz et al., (1988) *Europ. J Cell. Biol.* 46:144–151. Alternatively, the ACE cells are plated in 35 mm dishes or 6 well cluster plates at a density of $5\text{–}10\times10^3$ cells per dish or well in 2 ml of medium as described in Gospodarowicz et al., (1986), supra. Ten-microliter aliquots of appropriate dilutions of each sample are then added to duplicate or triplicate wells in the dishes on days 0 and 2. After 4 or 5 days in culture, the plates are trypsinized and cell densities determined in a Coulter counter. For purposes of description herein, a factor is considered to have mitogenic activity for vascular endothelial cells if the cell density at the end of this assay is at least 1.5 times and preferably at least 3 times the cell density of control wells receiving no factor additions.

The CKI polypeptide and endothelialization polypeptide can be co-delivered as, for example, purified protein mixtures. The proteins can be admixed prior to administration, or administered separately but in close temporal proximity to one and other.

Alternatively, one or both of the polypeptides can be delivered by a gene therapy vector. Where both are delivered by expression vectors, the coding sequences for each polypeptide can be present on the same expression construct, or can be provided by two separate constructs, the latter requiring co-transfection with both constructs. In the instance of the former, the coding sequences for each polypeptide can be under the control of the same promoter, and may even provide for a polycistronic message (see, for example, U.S. Pat. No. 4,713,339); alternatively, the two coding sequences, while present on the same expression vector can be under the control of two separate promotes.

The CKI polypeptide can consist of as little as a CDK-binding moitey of a CKI protein, or can include a full length CKI protein and/or be a poly-CBM protein.

(vii) Exemplary Pharmaceutical Preparations

For certain of the therapeutic uses of the subject chimeric proteins, particularly cutaneous uses such as for the control of keratinocyte proliferation, direct administration of the protein will be appropriate (rather than use of a gene therapy construct). Accordingly, the subject CKI polypeptide formulations may be conveniently formulated for administration with a biologically acceptable medium, such as water, buffered saline, polyol (for example, glycerol, propylene glycol, liquid polyethylene glycol and the like) or suitable mixtures thereof. In preferred embodiments, the chimeric protein is dispersed in lipid formulations, such as miscelles, which closely resemble the lipid composition of natural cell membranes to which the chimeric protein is to be delivered.

The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the CKI polypeptide (or internalization peptide or endothelialization polypeptide as the case may be), its use in the pharmaceutical preparation of the invention is contemplated. Suitable vehicles and their formulation inclusive of other proteins are described, for example, in the book Remington's Pharmaceutical Sciences (Remington's Pharmaceutical Sciences. Mack Publishing Company, Easton, Pa., USA 1985).

In an exemplary embodiment, the subject CKI protein mixture is provided for transmucosal or transdermal delivery. For such administration, penetrants appropriate to the barrier to be permeated are used in the formulation with the polypeptide. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the proteins of the invention are formulated into ointments, salves, gels, or creams as generally known in the art.

In accordance with the subject method, expression constructs of the subject CKI polypeptides (and endothelialization polypeptide as appropriate) may be administered in any biologically effective carrier, e.g. any formulation or composition capable of effectively transfecting cells in vivo with a recombinant fusion gene. Approaches include insertion of the subject fusion gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid encoding one of the subject CKI polypeptides into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a CKI polypeptide, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. Nos. 4,868,116; 4,980,286; PCT Application WO 89/07136; PCT Application WO 89/02468; PCT Application WO 89/05345; and PCT Application WO 92/07573).

In choosing retroviral vectors as a gene delivery system for the subject fusion proteins, it is important to note that a prerequisite for the successful infection of target cells by most retroviruses, and therefore of stable introduction of the recombinant gene, is that the target cells must be dividing. In general, this requirement will not be a hindrance to use of retroviral vectors to deliver the subject fusion gene constructs. In fact, such limitation on infection can be beneficial in circumstances where the tissue (e.g. nontransformed cells) surrounding the target cells does not undergo extensive cell division and is therefore refractory to infection with retroviral vectors.

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) PNAS 86:9079–9083; Julan et al. (1992) J. Gen Virol 73:3251–3255; and Goud et al. (1983) Virology 163:251–254); or coupling cell surface ligands to the viral env proteins (Neda et al. (1991) J Biol Chem 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue- or cell-specific transcriptional regulatory sequences which control expression of the fusion gene of the retroviral vector.

Another viral gene delivery system useful in the present invention utililizes adenovirus-derived vectors. The genome of an adenovirus can be manipulated such that it encodes a gene product of interest, but is inactivate in terms of its ability to replicate in a normal lytic viral life cycle (see, for example, Berkner et al. (1988) BioTechniques 6:616; Rosenfeld et al. (1991) Science 252:431–434; and Rosenfeld et al. (1992) Cell 68:143–155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including endothelial cells (Lemarchand et al. (1992) Proc. Natl. Acad. Sci. USA 89:6482–6486), and smooth muscle cells (Quantin et al. (1992) Proc. Natl. Acad. Sci. USA 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) Cell 16:683; Berkner et al., supra; and Graham et al. in *Methods in Molecular Biology*, E. J. Murray, Ed. (Humana, Clifton, N.J., 1991) vol. 7. pp. 109–127). Expression of the inserted fusion gene can be under control of, for example, the E1A promoter, the major late promoter (MLP) and associated leader sequences, the E3 promoter, or exogenously added promoter sequences.

Yet another viral vector system useful for delivery of the subject CKI polypeptides is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97–129). It is also one of the few viruses that may integrate its DNA into non-dividing cells, and exhibits a high frequency of stable integration (see for example Flotte et al. (1992) Am. J. Respir. Cell. Mol. Biol. 7:349–356; Samulski et al. (1989) J. Virol. 63:3822–3828; and McLaughlin et al. (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) Proc. Natl. Acad. Sci. USA 81:6466–6470; Tratschin et al. (1985) Mol. Cell. Biol. 4:2072–2081; Wondisford et al. (1988) Mol. Endocrinol. 2:32–39; Tratschin et al. (1984) J. Virol. 51:611–619; and Flotte et al. (1993) J. Biol. Chem. 268:3781–3790).

Other viral vector systems that may have application in gene therapy have been derived from herpes virus, vaccinia virus, and several RNA viruses. In particular, herpes virus vectors may provide a unique strategy for persistent expression of the subject fusion proteins in cells of the central nervous system and ocular tissue (Pepose et al. (1994) Invest Ophthalmol Vis Sci 35:2662–2666).

In addition to viral transfer methods, such as those illustrated above, non-viral methods can also be employed to cause expression of a the subject proteins in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the gene by the targeted cell. Exemplary gene delivery systems of this type include liposomal derived systems, poly-lysine conjugates, and artificial viral envelopes.

In a representative embodiment, a gene encoding one of the subject proteins can be entrapped in liposomes bearing positive charges on their surface (e.g., lipofectins) and (optionally) which are tagged with antibodies against cell surface antigens of the target tissue (Mizuno et al. (1992) No Shinkei Geka 20:547–551; PCT publication WO091/06309; Japanese patent application 1047381; and European patent publication EP-A-43075). For example, lipofection of neuroglioma cells can be carried out using liposomes tagged with monoclonal antibodies against glioma-associated antigen (Mizuno et al. (1992) Neurol. Med. Chir. 32:873–876).

In yet another illustrative embodiment, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, the subject gene construct can be used to transfect hepatocytic cells in vivo using a soluble polynucleotide carrier comprising an asialoglycoprotein conjugated to a polycation, e.g. poly-lysine (see U.S. Pat. No. 5,166,320). It will also be appreciated that effective delivery of the subject nucleic acid constructs via receptor-mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al. (1993) Science 260–926; Wagner et al. (1992) PNAS 89:7934; and Christiano et al. (1993) PNAS 90:2122).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057).

Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral packages, the pharmaceutical preparation can comprise one or more cells which produce the gene delivery system. In the case of the latter, methods of introducing the viral packaging cells may be provided by, for example, rechargeable or biodegradable devices. Various slow release polymeric devices have been developed and tested in vivo in recent years for the controlled delivery of drugs, including proteinacious biopharmaceuticals, and can be adapted for release of viral particles through the manipulation of the polymer composition and form. A variety of biocompatible polymers (including hydrogels), including both biodegradable and non-degradable polymers, can be used to form an implant for the sustained release of an the viral particles by cells implanted at a particular target site. Such embodiments of the present invention can be used for the delivery of an exogenously purified virus, which has been incorporated in the polymeric device, or for the delivery of viral particles produced by a cell encapsulated in the polymeric device.

By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, Concise Encyclopedia of Medical & Dental Materials, ed. by David Williams (MIT Press: Cambridge, Mass., 1990); and the Sabel et al. U.S. Pat. No. 4,883,666. In another embodiment of an implant, a source of cells producing the recombinant virus is encapsulated in implantable hollow fibers. Such fibers can be pre-spun and subsequently loaded with the viral source (Aebischer et al. U.S. Pat. No. 4,892,538; Aebischer et al. U.S. Pat. No. 5,106,627; Hoffman et al. (1990) Expt. Neurobiol. 110:39–44; Jaeger et al. (1990) Prog. Brain Res. 82:41–46; and Aebischer et al. (1991) J. Biomech. Eng. 113:178–183), or can be co-extruded with a polymer which acts to form a polymeric coat about the viral packaging cells (Lim U.S. Pat. No. 4,391,909; Sefton U.S. Pat. No. 4,353,888; Sugamori et al. (1989) Trans. Am. Artif. Intern. Organs 35:791–799; Sefton et al. (1987) Biotechnol. Bioeng. 29:1135–1143; and Aebischer et al. (1991) Biomaterials 12:50–55). Again, manipulation of the polymer can be carried out to provide for optimal release of viral particles.

(viii) Exemplary Uses for the Subject Antiproliferative Formulations

The subject fusion proteins can be used in the treatment of hyperproliferative vascular disorders, e.g. smooth muscle hyperplasia (such as atherosclerosis) or restinosis, as well as other disorders characterized by fibrosis, e.g. rheumatoid arthritis, insulin dependent diabetes mellitus, glomerulonephritis, cirrhosis, and scleroderma, particularly proliferative disorders in which loss of TGF-β autocrine or paracrine signaling, and accordingly loss of p15 function, is implicated.

For example, restinosis continues to limit the efficacy of coronary angioplasty despite various mechanical and pharmaceutical interventions that have been employed. An important mechanism involved in normal control of intimal proliferation of smooth muscle cells appears to be the induction of autocrine and paracrine TGF-β inhibitory loops in the smooth muscle cells (Scott-Burden et al. (1994) Tex Heart Inst J 21:91–97; Graiger et al. (1993) Cardiovasc Res 27:2238–2247; and Grainger et al. (1993) Biochem J 294:109–112). Loss of sensitivity to TGF-β, or alternatively, the overriding of this inhibitory stimulus such as by PDGF autostimulation, can be a contributory factor to abnormal smooth muscle proliferation in restinosis. It may therefore be possible to treat or prevent restinosis by the use of gene therapy with CDK inhibitor fusion protein of the present invention. The fusion gene construct can be delivered, for example, by percutaneous transluminal gene transfer (Mazur et al. (1994) Tex Heart Inst J 21:104–111) using viral or liposomal delivery compositions. An exemplary adenovirus-mediated gene transfer technique and compositions for treatment of cardiac or vascular smooth muscle is provided in PCT publication WO 94/11506.

In one embodiment, the co-delivery of a CKI polypeptide with an endothelization polypeptide can be used in the treatment of disorders/injury marked by unwanted smooth muscle cell proliferation and deepithelialization. For example, the co-administration approach can be used as a post-operative wound healing agent in balloon angioplasty, a procedure in which vascular endothelial cells are removed or damaged, together with compression of atherosclerotic plaques. The two polypeptides can be co-delivered to inner vascular surfaces by systemic or local intravenous application either as intravenous bolus injection or infusions of polypeptides, expression constructs, or a mixture thereof. If desired, the endothelialization polypeptide can be administered over time using a micrometering pump, while the CKI polypeptide is ultimately delivered by gene therapy. Suitable compositions for intravenous administration comprise the endothelization polypeptide in an amount effective to promote endothelial cell growth and a parenteral carrier material. The endothelization polypeptide can be present in the composition over a wide range of concentration, administered once or in dosing regimens that allow for multiple applications. Any of the known parenteral carrier vehicles can be used, such as normal saline or 5–10% dextrose.

The co-delivery embodiment of the subject method can also be used to inhibit SMC proliferation yet promote endothelialization in vascular graft surgery. In the case of vascular grafts using either transplanted vessels or synthetic material, for example, the endothelization polypeptide can be applied to the surfaces of the graft and/or at the junctions of the graft and the existing vasculature in order to promote the growth of vascular endothelial cells. For such applications, the endothelization polypeptide can be applied intravenously as described above for balloon angioplasty or it can be applied directly to the surfaces of the graft and/or the existing vasculature either before or during surgery.

Transforming growth factor-β is also understood to play a significant role in local glomerular and interstitial sites in human kidney development and disease. Consequently, the subject method provides a method of treating or inhibiting glomerulopathies and other renal proliferative disorders comprising the in vivo delivery and recombinant expression of the subject fusion proteins, e.g., the poly-CBM and/or transcellular CKI polypeptides, in kidney tissue.

In other embodiments, therapeutic application of a CDK inhibitor fusion protein, e.g., by gene therapy, can be used in the treatment of a neuroglioma. Gliomas account for 40–50% of intracranial tumors at all ages of life. Despite the increasing use of radiotherapy, chemotherapy, and sometimes immunotherapy after surgery for malignant glioma, the mortality and morbidity rates have not substantially improved. However, there is increasing experimental and clinical evidence that for a significant number of gliomas, loss of TGF-β responsiveness is an important event in the loss of growth control. Irrespective of the cause of decreased responsiveness, e.g. the loss of function of p15 or the loss of other TGF-β signal transduction proteins, exogenous expression of, for example, an INK4 fusion protein such as p15/p27 fusion protein in the cell can used effectively to inhibit cell proliferation.

Yet another aspect of the invention pertains to methods of treating proliferative and/or differentiative disorders which arise from cells which, despite aberrant growth control, still require one or more CDKs (e.g., CDK4 or CDK6) for cell growth. There are a wide variety of pathological cell proliferative conditions for which the fusion gene constructs of the present invention can provide therapeutic benefits, with the general strategy being the inhibition of an anomalous cell proliferation. For instance, the gene constructs of the present invention can be used as a part of a gene therapy protocol in a cell in which a cell-cycle regulatory protein (such as an INK4 or CIP protein) is misexpressed or in which signal transduction pathways upstream of the protein are dysfunctional. To illustrate, cell types which exhibit pathological or abnormal growth presumably dependent at least in part on a function of a, INK4 or CIP protein include various cancers and leukemias, psoriasis, bone diseases, fibroproliferative disorders such as involving connective tissues, atherosclerosis and other smooth muscle proliferative disorders, as well as chronic inflammation. In addition to proliferative disorders, the treatment of differentiative disorders which result from, for example, de-differentiation of tissue which may (optionally) be accompanied by abortive reeentry into mitosis. Such degenerative disorders include chronic neurodegenerative diseases of the nervous system, including Alzheimer's disease, Parkinson's disease, Huntington's chorea, amylotrophic lateral sclerosis and the like, as well as spinocerebellar degenerations. Other differentiative disorders include, for example, disorders associated with connective tissue, such as may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors. It will also be apparent that, by transient use of gene therapy constructs of the subject fusion proteins, in vivo reformation of tissue can be accomplished, e.g. in the development and maintenance of organs. By controlling the proliferative and differentiative potential for different cells, the subject gene constructs can be used to reform injured tissue, or to improve grafting and morphology of transplanted tissue. For example, the subject CDK inhibitors can be employed therapeutically as part of a regimen to regulate organs after physical, chemical or pathological insult.

Furthermore, as described in the art, transformation of a cell can be due in part to a loss-of-function mutation to a particular INK4 gene, e.g., ranging from a point mutation to gross deletion of the gene. Additionally, other data suggests that certain disorders may arise because cells have lost the ability to induce expression of an INK4 gene. Normal cell proliferation, for instance, is generally marked by responsiveness to negative autocrine or paracrine growth regulators, such as members of the TGF-β family, e.g. TGF-β1, TGF-β2 or TGF-β3, and related polypeptide growth inhibitors. Ordinarily, control of cellular proliferation by such growth regulators, particularly in epithelial and hemopoietic cells, is in the form of growth inhibition. Moreover, as described in Hannon and Beach (1995) Nature 371:257–261, TGF-β inhibits cell proliferation by inducing expressions of p15, which in turn inhibits activation of CDK4 or CDK6 complexes.

It has been observed that a significant percentage of human cancers derived from cells types ordinarily inhibited by TGF-β display a reduced responsiveness to this growth regulator. For instance, some tumors of colorectal, liver epithelial, and epidermal origin show reduced sensitivity and resistance to the growth-inhibitory effects of TGF-β as compared to their normal counterparts. In this context, a noteworthy characteristic of several retinoblastoma cell lines is the absence of detectable TGF-β receptors. Treatment of such tumors with the subject fusion proteins provides an opportunity to mimic the TGF-β inhibitory signal. Moreover, it will be appreciated that the subject method can be used generally to inhibit proliferation of cells which, in general, are still reliant on cyclin dependent kinases.

It has been demonstrated that gene therapy can be used to target glioma cells for expression of recombinant proteins (Miyao et al. (1993) J. Neurosci. Res. 36:472–479; Chen et al. (1994) PNAS 91:3054–3057; and Takamiya et al. (1993) J. Neurosurg. 79:104–110). Thus, a gene construct for expressing the subject fusion protein can be delivered to the tumor, preferably by sterotactic-dependent means. In preferred embodiments, the gene delivery system is a retroviral vector. Since rapidly growing normal cells are rare in the adult CNS, glioma cells can be specifically transduced with a recombinant retrovirus. For example, the retroviral particle can be delivered into the tumor cavity through an Ommaya tube after surgery, or alternatively, packaging fibroblasts encapsulated in retrievable immunoisolatory vehicles can be introduced into the tumor cavity. In order to increase the effectiveness and decrease the side effects of the retrovirus-mediated gene therapy, glioma-specific promoters can be used to regulate expression of the therapeutic gene. For example, the promoter regions of glial fibrillary acidic protein (GFAP) and myelin basis protein (MBP) can operably linked to the fusion gene in order to direct glial cell-specific expression of the fusion protein.

In another embodiment, gene therapy can be used in conjunction with the subject fusion proteins in the treatment of various carcinomas. In a representative embodiment, a gene therapy system comprising the subject fusion gene is used to treat certain breast cancers. In preferred embodiments, expression of the subject fusion protein is controlled at least in part by a mammary-specific promoter, a number of which are available (for review, see Hennighausen (1990) Protein Expression and Purification 1:3–8; and Günzberg et al. (1992) Biochem J 283:625–632).

In similar fashion, gene therapy protocols involving delivery of the subject fusion protein can be used in the treatment of malignant melanoma, which also serves as a model for progressive TGF-β resistance in transformation. In preferred embodiments, gene therapy protocols for treatment of melanomas include, in addition to the delivery of the fusion gene construct, the delivery of a pharmaceutical preparation of the gene by direct injection. For instance, U.S. Pat. No. 5,318,514 describes an applicator for the electroporation of genes into epidermal cells and can be used in accordance with the present invention.

The subject method can also be used to treat retinoblastomas in which the retinoblastoma gene (RB) is not itself impaired, e.g. the effective impairment of the RB checkpoint is the result of a failure to control CDK4 phosphorylation of RB. Thus, one of the subject fusion proteins can be expressed in a retinoblastoma cell, thereby causing inhibition of CDK4 activation and down-regulating RB phosphorylation. To illustrate, a recombinant retrovirus can be constructed to facilitate expression of a fusion protein including an INK4 protein, e.g., derived from p16 or p15, and a CIP protein, e.g., derived from p21, p27 or p57. Infectivity of retinoblastoma cells can be enhanced by derivatizing the env protein with antibodies specific for retinoblastoma cells, e.g. antibodies to retinal S-antigen (Doroso et al. (1985) Invest Opthalmol Vis Sci 26:560–572; see also Liao et al. (1981) Eur J Immunol 11:450–454; and U.S. Pat. No. 4,444,744).

In yet another embodiment, the subject gene is delivered to a sarcoma, e.g. an osteosarcoma or Kaposi's sarcoma. In a representative embodiment, the gene is provided in a viral vector and delivered by way of a viral particle which has been derivatized with antibodies immunoselective for an osteosarcoma cell (see, for example, U.S. Pat. Nos. 4,564,517 and 4,444,744; and Singh et al. (1976) Cancer Res 36:4130–4136).

Given the role of CDK activation in various epithelial cell proliferative disorders, it will be evident that the subject fusion proteins will find ready application for the treatment or prophylaxis of, for example, psoriasis; keratosis; acne; comedogenic lesions; verrucous lesions such as verruca plana, plantar warts, verruca acuminata, and other verruciform lesions marked by proliferation of epithelial cells; folliculitis and pseudofolliculitis; keratoacanthoma; callosities; Darier's disease; ichthyosis; lichen planus; molluscous contagiosum; melasma; Fordyce disease; and keloids or hypertrophic scars.

Yet another aspect of the present invention relates to the use of the subject fusion proteins to control hair growth. The growth of hard keratin fibers such as wool and hair is dependent on the proliferation of dermal sheath cells. Hair follicle stem cells of the sheath are highly active, and give rise to hair fibers through rapid proliferation and complex differentiation. The hair cycle involves three distinct phases: anagen (growing), catagen (regressing), and telogen (resting). The epidermal stem cells of the hair follicle are activated by dermal papilla during late telogen. This is termed "bulge activation". Moreover, such stem cells are thought to be pluripotent stem cells, giving rise not only to hair and hair follicle structures, but also the sebaceous gland and epidermis. The subject method provides a means for altering the dynamics of the hair growth cycle to induce quiescence of proliferation of hair follicle cells, particularly stem cells of the hair follicle, inhibiting CDK activation.

For instance, gene therapy treatments or, alternatively, topical administration of a fusion protein preparation, can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, the subject fusion proteins can be used to manage hirsutism, a disorder marked by abnormal hairiness. Application of the CDK inhibitors of the present invention can also provide a process for extending the duration of depilation.

Moreover, because the CDK inhibitor fusion proteins are likely to be cytostatic to epithelial cells, rather than cytotoxic, these proteins can be used to protect hair follicle cells from cytotoxic agents which require progression into S-phase of the cell-cycle for efficacy, e.g. radiation-induced death. Treatment with a CDK inhibitor of the present invention provides protection by causing the hair follicle cells to become quiescent, e.g., by inhibiting the cells from entering S phase, and thereby preventing the follicle cells from undergoing mitotic catastrophe or programmed cell death. For instance, such treatments can be used for patients undergoing chemo- or radiation-therapies which ordinarily result in hair loss.

The subject method can also be used in the treatment of folliculitis, such as folliculitis decalvans, folliculitis ulerythematosa reticulata or keloid folliculitis. For example, a cosmetic prepration of an CDK inhibitory fusion protein can be applied topically in the treatment of pseudofolliculitis, a chronic disorder occurring most often in the submandibular region of the neck and associated with shaving, the characteristic lesions of which are erythematous papules and pustules containing buried hairs.

In similar fashion, such preparations can be used in the treatment of granulomas, e.g. tumor-like mass or nodule of granulation tissue, which may include epithelial tissue derived from cutaneous or mucosal sources.

In another aspect of the invention, the subject method can be used in conjunction with various periodontal procedures in which inhibition of epithelial cell proliferation in and around periodontal tissue is desired. For example, preparations of the present invention can find application in the treatment of peridontal disease. It is estimated that in the United States alone, there are in excess of 125 million adults with periodontal disease in varying forms. Periodontal disease starts as inflammatory lesions because of specific bacteria localizing in the area where the gingiva attaches to the tooth. Usually first to occur is a vascular change in the underlying connective tissue. Inflammation in the connective tissue stimulates the following changes in the epithelial lining of the sulcus and in the epithelial attachment: increased mitotic activity in the basal epithelial layer; increased producing of keratin with desquamation; cellular desquamation adjacent to the tooth surface tends to deepen the pocket; epithelial cells of the basal layer at the bottom of the sulcus and in the area of attachment proliferate into the connective tissue and break up of the gingival fibers begins to occur, wherein dissolution of the connective tissue results in the formation of an open lesion. The application of CDK inhibitor preparations to the periodontium can be used to inhibit proliferation of epithelial tissue and thus prevent further periodontoclastic development.

In yet another embodiment of the present invention, the subject CDK inhibitors can be used to inhibit spermatogenesis or oogenesis by inhibiting progression through mitotic or meiotic cell-cycle stages. The anti-mitotic and/or anti-meiotic activity of the fusion proteins identified in the present invention may accordingly be used, for example, in birth control methods by disrupting oogenic pathways in order to prevent the development of either the egg or sperm, or by preventing mitotic progression of a fertilized egg.

In a still further embodiment, the subject fusion protein is recombinantly expressed in tissue which is characterized by unwanted de-differentiation and which may also be undergoing unwanted apoptosis. For instance, many neurological disorders are associated with degeneration of discrete populations of neuronal elements. For example, Alzheimer's disease is associated with deficits in several neurotransmitter systems, both those that project to the neocortex and those that reside with the cortex. For instance, the nucleus basalis in patients with Alzheimer's disease were observed to have a profound (75%) loss of neurons compared to age-matched controls. Although Alzheimer's disease is by far the most common form of dementia, several other disorders can produce dementia. Many are age-related, occurring in far greater incidence in older people than in younger. Several of these are degenerative diseases characterized by the death of neurons in various parts of the central nervous system, especially the cerebral cortex. However, some forms of dementia are associated with degeneration of the thalamus or the white matter underlying the cerebral cortex. Here, the cognitive dysfunction results from the isolation of cortical areas by the degeneration of efferents and afferents. Huntington's disease involves the degeneration of intrastriatal and cortical cholinergic neurons and GABAergic neurons. Pick's disease is a severe neuronal degeneration in the neocortex of the frontal and anterior temporal lobes, sometimes accompanied by death of neurons in the striatum. Accordingly, the subject fusion proteins can be delivered to the effected tissue by gene therapy techniques. It is noted that numerous advances have been made in the construction of expression vectors, cellular and viral transgene carriers, and the characterization of target cells for neuronal gene therapy, and can be readily adapted for delivery of the subject genes (see, for example, Suhr et al. (1993) Arch Neurol 50:1252–1268; Jiao et al. (1993) Nature 362:450–453; Friedmann (1992) Ann Med 24:411–417; and Freese et al. (1991) Nuc Acid Res 19:7219–7223).

In addition to degenerative-induced dementias, the subject gene therapy systems can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. Moreover, the use of the subject fusion gene therapy constructs is amenable to the treatment of disorders of the cerebellum which result in hypotonia or ataxia, such as those lesions in the cerebellum which produce disorders in the limbs ipsilateral to the lesion. For instance, p16/p27 fusion gene constructs can used to treat a restricted form of cerebellar cortical degeneration involving the anterior lobes (vermis and leg areas) such as is common in alcoholic patients.

Furthermore, the subject fusion proteins can also be used in the treatment of autonomic disorders of the peripheral nervous system, which include disorders affecting the innervation of smooth muscle and endocrine tissue (such as glandular tissue). For instance, recombinant fusion protein of the present invention can be expressed by gene therapy and used to treat tachycardia or atrial cardiac arrythmias which may arise from a degenerative condition of the nerves innervating the striated muscle of the heart.

As will be apparent, the subject gene constructs can be used to cause expression of the fusion polypeptides in cells propagated in culture, e.g. to produce proteins or polypeptides, including fusion proteins or polypeptides, for purification. In addition, recombinant expression of the subject fusion polypeptides in cultured cells can be useful for controlling differentiation states of cells in vitro, for instance, by controlling the level of activation of a CDK. To illustrate, in vitro neuronal culture systems have proved to be fundamental and indispensable tools for the study of neural development, as well as the identification of neurotrophic factors. Once a neuronal cell has become terminally-differentiated, it typically will not change to another terminally differentiated cell-type. However, neuronal cells can nevertheless readily lose their differentiated state. This is commonly observed when they are grown in culture from adult tissue, and when they form a blastema during regeneration. By preventing the activation of one or more CDKs, particularly in $G_0$ or $G_1$, certain of the subject fusion proteins can prevent mitotic progression and hence provide a means for ensuring an adequately restrictive environment in order to maintain neuronal cells at various stages of differentiation, and can be employed, for instance, in cell cultures designed to test the specific activities of trophic factors. Other tissue culture systems which require maintenance of differentiation will be readily apparent to those skilled in the art. In this respect, each of the subject antagonist of CDK4 activation can be used for ex vivo tissue generation, as for example, to enhance the generation of prosthetic tissue devices for implantation. That is, by inhibiting the activation of a CDK with one of the subject fusion proteins, cultured cells can be guided along certain differentiative pathways.

EXEMPLIFICATION

The invention now being generally described, it will be more readily understood by reference to the following examples which are included merely for purposes of illustration of certain aspects and embodiments of the present invention, and are not intended to limit the invention.

Prototype embodiments of the CDK inhibitory fusion protein described above were derived from the fusion of the coding sequences from the human p27 and p16 cDNAs. The nucleotide sequence for the fusion gene encoding the p27-p16 protein is provided in SEQ ID No. 1, with the corresponding amino acid sequence being designated by SEQ ID No. 2. The construct includes a poly(His) leader for purification, along with a hinge region including a $(Gly_4Ser)_3$ linker to permit proper folding and breathing of each of the p27 and p16 portions of the resulting protein. The sequences for both human p27 and human p16 have been described in the art. Briefly, the p27-p16 fusion protein was constructed as follow.

The expression vector is pT7-7 from US Biocehmical. To construct the p27-p16 fusion, first we PCR amplified the p27 coding sequence using the following primers:

N-terminal primer: (SEQ ID No. 3)

```
5'-GCGGCCGGTCATATGCACCACCATCACCATCACTCAAACG-
TGCGAGTGTCT-3'
```

This primer carries an Ndel site and 6 histidine codons that are inserted between the ATG and the second amino acid of p27.

C-terminal primer: (SEQ ID No. 4)

```
5'-GCCGCCGGCGTCGACTCGGCCGAATTCGGATCCACCCCCGCCGGAA-
CCGCCACCCCCGCTGCCCCCGCCACCCGTTTGACGTCTTCTGAGGCCAG-
G-3'
```

This primer carries the $(Gly_4Ser)_3$ repeat and EcoR1, Sal1 and Hind3 restriction sites and eliminates the stop codon of p27.

The p27 PCR product was cut with Ndel and Hind3 and inserted into pT7–7 cut with Ndel and Hind3. The resulted construct was cut with EcoR1 and Sal1 and a full length p16 PCR product was inserted as an EcoR1-Xho1 fragment. The position of the EcoR1 site allows the in-frame insertion of p16. The rest of the hinge region between the p27 and p16 coding sequences derives from the 5' end of the p16 cDNA.

The pT7p27-p16 expression plasmid was transformed into BL21 cells. For fusion protein expression, cells were grown in LB+50 $\mu$g/ml ampicillin at 37 C. to $OD_{600}$=0.8 and protein expression was induced by IPTG (final; conc.: 20 mM) for 4 hours as 37 C. Cells were collected and the pellet was frozen at −80 C. The preparation of the cell lysate and binding to a $Ni^{2+}$ charged SEPHAROSE resin (Invitrogen catalog no. R801) was done according to the manufacturer's instruction (Invitrogen; see also Hochuli et al. (1987) J. Chromatography 411:177–184; and Janknecht et al. (1991) PNAS 88:8972–8976). The bound proteins were eluted with 50 mM, 200 mM, 350 mM, and 500 mM imidazol and the fractions were analyzed on SDS/PAGE. The 200 mM, 350 mM, and 500 mM imidazol fractions were collected, dialised against 1×PBS(1 mM $KH_2PO_4$, 10 mM $Na_2HPO_4$, 137 mM NaCl, 2.7 mM KCl, pH=7.4)+10% glycerol and stored at −80 C. in aliquots. ~25% of the prep was the fusion protein.

The purity of the p27-p16, p27, and p16 preperationss were normalized using p16 and p27 specific antibodies.

The kinase inhibitory activity of the p27-p16 fusion protein was determined using an in vitro kinase assay in which the kinase activity of a particular cyclin/CDK complex was measured for varying concentrations of fusion protein. Briefly, the assay employs Sf9 cell extracts that were made from cells that were coinfected with the proper CDK and cyclin expression constructs. Typically, 44 μg of Sf9 extract in 50 μl of 50 mM Tris/Cl pH=7.6, 10 mM $MgCl_2$, 1 mM DTT, 25 μM ATP, 10 μCi $^{32}P$-γ-ATP was used in the absence of the presnce of the particular inhibitor (inhibitor concentration was between 25 nM to 1 μM). The reaction was carried out at 30° C. for 30 minutes using 2 μg of Gst-Rb as a substrate. Gst-Rb was recaptured using GSH-agaraose, separated on 10% SDS/PAGE and stained with Comassie blue. After autoradiography the GST-Rb bands were cut out and $^{32}P$ incorporation was measured.

The concentration of p27-p16 fusion protein at which 50% of the kinase activity was blocked ($IC_{50}$) was calculated for various cyclin/CDK pairs. The results are indicated in Table I.

TABLE I

Inhibition of cyclin dependent kinase complexes by p27-p16 fusion protein

| inhibitor | CDK4/cycl in Dl | CDK2/cycl in E | CDK2/cycl in A | cdc2/cyclin B |
|---|---|---|---|---|
| p27-p16 | 25 nm | 30 nm | 25 nm | 15 nm |
| p27 | 63 nm | 52 nm | 65 nm | 20 nm |
| p16 | 250 nm | >500 nm | >500 nm | >500 nm |

nm = nanomolar

Moreover, the inhibition constant, $K_i$ for the inhibition of CDK4/cyclin D1 by p27-p16 fusion protein was determined to be 23 nm, compared to a $K_i$ of 75 nm for p16 inhibition of the same CDK4 complex.

Other exemplary fusion proteins were derived as follows:

(i) a "p16(GS)p27" fusion protein was generated to include, N to C terminal, the entire coding sequence of p16, fused in frame with a $(Gly_4Ser)_3$ linker and then the full coding sequence of p27. The nucleotide sequence for the fusion gene encoding the p16(GS)p27 protein is provided in SEQ ID No:5, with the corresponding amino acid sequence being designated by SEQ ID No:6; and (ii) a "p16p27" fusion protein was generated to include, N to C terminal, the entire coding sequence of p16, fused in frame the full coding sequence of p27 (no $(Gly_4Ser)_3$ linker). The nucleotide sequence for the fusion gene encoding the p16p27 protein is provided in SEQ ID No:7, with the corresponding amino acid sequence being designated by SEQ ID No:8.

In other embodiments, we have constructed fusion inhibitors that contain smaller portions of p27. In these p27 derivatives we have deleted sequences that may play a role in p27 degradation. The idea here that we may increase in vivo efficacy by increasing potency and stability, e.g., by rendering the fusion resistant to ubiquitin-mediated degradation. The truncated p27 protein (12aa–177aa) is SEQ ID No:18, which provides a polypeptide of the formula EcoR1-ATG-HA epitope-p27(12aa–177aa)-Stop-Not1 . Still another truncated variant of p27 is provided in SEQ ID No:19, and encodes a polypeptide of the formula EcoR1-ATG-HA epitope-p27(25aa–97aa)-STOP-Not1 SEQ ID No:20.

Utilizing these p27 fragments, we have constructed p27/p16 fusion proteins of the formula EcoR1-ATG-HA epitope-p27(12aa–177aa)-p16(2aa–155aa)-STOP-Not1, which is shown in SEQ ID Nos:21 and 22, and of the formula EcoR1-ATG-HA epitope-p27(12aa–177aa)-$(Gly_4Ser)_3$ hinge-p16((2aa–155aa)-STOP-Not1, shown in SEQ ID Nos:23 and 24.

Still other p27/p16 fusion with the truncated p27 is EcoR1-ATG-HA epitope-p27(25aa–93aa)-p16(2aa–155aa)-STOP-Not1, shown in SEQ ID Nos:25 and 26, and EcoR1-ATG-HA epitope-p27(25aa–93aa)-$(Gly_4Ser)_3$ hinge-p16 (2aa–155aa)-STOP-Not1, shown in SEQ ID Nos:27 and 28.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A nucleic acid encoding a fusion protein comprising a therapeutic polypeptide sequence comprising CDK-binding motifs from two or more proteins that bind to cyclin-dependent kinases, and a transcellular polypeptide sequence for promoting transcytosis of the fusion protein across a cell surface membrane and into a cell, wherein the therapeutic polypeptide sequence inhibits one or more cyclin-dependent kinases upon intracellular localization of the fusion protein.

2. A gene delivery composition a recombinant viral particle including a nucleic acid of claim 1.

3. A gene delivery composition comprising a nucleic acid of claim 1, wherein the gene delivery composition is a liposome or a poly-cationic nucleic acid binding agent.

4. A gene delivery composition comprising a nucleic acid of claim 1, wherein the gene delivery composition further comprises a pharmaceutically acceptable carrier for administration to an animal.

5. The method of claim 1, wherein the fusion protein further comprises a signal secretion sequence.

6. The nucleic acid of claim 1, wherien said therapeutic polypeptide sequence is selected from p27-p16, p16(GS) p27, EcoR1-ATG-HA epitope-p27(12aa–177aa)-($GLY_4$ $Ser)_3$- hinge-p16(2aa–155aa)-STOP-Not1, EcoR1-ATG-HA epitope-p27(12aa–177aa)-p16(2aa–155aa)- STOP-Not1, EcoR1-ATG-HA epitope-p27(25aa–93aa)-p16(2aa–155aa)-STOP-Not1, or EcoR1- ATG-HA epitope-p27(25aa–93aa)-($Gly_4Ser)_3$-hinge-p16(2aa–155aa)-STOP-Not1.

7. The nucleic acid of claim 1, wherein said therapeutic polypeptide sequence is p27-p16.

8. The nucleic acid of claim 1, wherein said therapeutic polypeptide sequence is EcoR1-ATG-HA epitope-p27 (12aa–177aa)-($Gly_4Ser)_3$-hinge-p16(2aa–155aa)-STOP-Not1.

9. The nucleic acid of claim 1, wherein said therapeutic polypeptide sequence is EcoR1-ATG-HA epitope-p27 (12aa–177aa)-p16(2aa–155aa)-STOP-Not1.

10. The nucleic acid of claim 1, wherein said therapeutic polypeptide sequence is EcoR1-ATG-HA epitope-p27 (25aa–93aa)-p16(2aa–155aa)-STOP-Not1.

11. The nucleic acid of claim 1, wherein said therapeutic polypeptide sequence is EcoR1-ATG-HA epitope-p27 (25aa–93aa)-($Gly_4Ser)_3$-hinge-p16(2aa–155aa)-STOP-Not1.

12. The nucleic acid encoding a fusion protein of claim 1, wherein the transcellular polypeptide sequence is an internalizing peptide.

13. The nucleic acid encoding a fusion protein of claim 12, wherein the internalizing peptide is a polypeptide selected from antennapedia protein, HIV transactivating (TAT) protein, mastoparan, melittin, bombolittin, delta hemolysin, pardaxin, Pseudomonas exotoxin A, clathrin, Diphtheria toxin, or C9 complement protein, or a fragment thereof.

14. The nucleic acid encoding a fusion protein of claim 12, wherein the internalizing peptide is antennapedia protein or a fragment thereof.

15. The nucleic acid encoding a fusion protein of claim 12, wherein the internalizing peptide is HIV transactivating (TAT) protein or a fragment thereof.

16. The nucleic acid encoding a fusion protein of claim 1, wherein the transcellular polypeptide sequence is an accessory peptide sequence which enhances interaction of the fusion protein with a cell surface membrane.

17. The nucleic acid encoding a fusion protein of claim 16, wherein the accessory peptide includes an RGD sequence.

18. A viral vector comprising a nucleic acid of claim 1.

19. The vector of claim 18, wherein the viral vector is an adenoviral vector.

20. The vector of claim 18, wherein the viral vector is an adeno-associated viral vector.

21. The vector of claim 18, wherein the viral vector is a retroviral vector.

22. A method for treating an animal for unwanted cell proliferation, comprising administering to the animal a transfection system comprising a nucleic acid encoding a fusion protein comprising a first polypeptide sequence comprising CDK-binding motifs from two or more proteins that inhibit a cyclin-dependent kinase, and a second transcellular polypeptide sequence selected from antennapedia protein, HIV transactivating (TAT) protein, mastoparan, melittin, bombolittin, delta hemolysin, pardaxin, Pseudomonas exotoxin A, clathrin, Diphtheria toxin, C9 complement protein, or fragments thereof.

23. The method of claim 22, wherein said first polypeptide sequence is selected from p27–p16, p16(GS)p27, EcoR1-ATG-HA epitope-p27(12aa–177aa)-($Gly_4Ser$)$_3$-hinge- p16 (2aa–155aa)-STOP-Not1, EcoR1-ATG-HA epitope-p27 (12aa–177aa)-p16(2aa–155aa)-STOP- Not1, EcoR1-ATG-HA epitope-p27(25aa–93aa)-p16(2aa–155aa)-STOP-Not1, or EcoR1-ATG- HA epitope-p27(25aa-–93aa)-($Gly_4Ser$)$_3$-hinge-p16(2aa–155aa)-STOP-Not1.

24. The method of claim 22, wherein said first polypeptide sequence is p27-p16.

25. The method of claim 22, wherein said first polypeptide sequence is p16(GS)P27.

26. The method of claim 22, wherein said first polypeptide sequence is EcoR1- ATG-HA epitope-p27(12aa–177aa)-($Gly_4Ser$)$_3$-hinge-p16(2aa–155aa)-STOP-Not1.

27. The method of claim 22, wherein said first polypeptide sequence is EcoR1- ATG-HA epitope-p27(12aa–177aa)-p16 (2aa–155aa)-STOP-Not1.

28. The method of claim 22, wherein said first polypeptide sequence is EcoR1- ATG-HA epitope-p27(25aa–93aa)-p16 (2aa–155aa)-STOP-Not1.

29. The method of claim 22, wherein said first polypeptide sequence is EcoR1- ATG-HA epitope-p27(25aa–93aa)-($Gly_4Ser$)$_3$-hinge-p16(2aa–155aa)-STOP-Not1.

30. The nucleic acid of claim 1, wherein the fusion protein further comprises a signal secretion sequence.

31. The method of claim 20, wherein the nucleic acid encoding the fusion protein is operably linked to a transcriptional regulatory sequence for causing expression of the fusion protein in eukaryotic cells.

32. A method for treating an animal for unwanted cell proliferation, comprising administering to the animal a transfection system comprising a nucleic acid encoding a fusion protein comprising a polypeptide sequence comprising CDK-binding motifs from two or more proteins that inhibit a cyclin-dependent kinase, and a transcellular polypeptide sequence.

33. The method of claim 32, wherein the nucleic acid encoding the fusion protein is operably linked to a transcriptional regulatory sequence for causing expression of the fusion protein in eukaryotic cells.

34. The method of claim 32, wherein said polypeptide sequence is selected from p27–p16, p16(GS)p27, EcoR1-ATG-HA epitope-p27(12aa–177aa)-($Gly_4Ser$)$_3$-hinge-p16 (2aa–155aa)-STOP-Not1, EcoR1-ATG-HA epitope-p27 (12aa–177aa)-p16(2aa–155aa)-STOP-Not1, EcoR1-ATG-HA epitope-p27(25aa–93aa)-p16(2aa–155aa)-STOP-Not1, or EcoR1-ATG-HA epitope-p27(25aa–93aa)-($Gly_4Ser$)$_3$-hinge-p16(2aa–155aa)-STOP-Not1.

35. The method of claim 32, wherein said polypeptide sequence is p27-p16.

36. The method of claim 32, wherein said polypeptide sequence is p16(GS)p27.

37. The method of claim 32, wherein said polypeptide sequence is EcoR1ATG- HA epitope-p27(12aa–177aa)-($Gly_4Ser$)$_3$-hinge-p16(2aa–155aa)-STOP-Not1.

38. The method of claim 32, wherein said polypeptide sequence is EcoR1ATG- HA epitope-p27(12aa–177aa)-p16 (2aa–155aa)-STOP-Not1.

39. The method of claim 32, wherein said polypeptide sequence is EcoR1-ATG- HA epitope-p27(25aa–93aa)-p16 (2aa–155aa)-STOP-Not1.

40. The method of claim 32, wherein said polypeptide sequence is EcoR1ATG- HA epitope-p27(25aa–93aa)-($Gly_4Ser$)$_3$-hinge-p16(2aa–155aa)-STOP-Not1.

41. The nucleic acid of claim 32, wherein the fusion protein further comprises a signal secretion sequence.

42. A nucleic acid encoding a fusion protein comprising a therapeutic polypeptide sequence comprising a p21/p27 inhibitory domain, and a transcellular polypeptide sequence for promoting transcytosis of the fusion protein across a cell surface membrane and into a cell, wherein the therapeutic polypeptide sequence inhibits one or more cyclin-dependent kinases upon intracellular localization of the fusion protein.

* * * * *

```
                    SEQUENCE LISTING


(1) GENERAL INFORMATION:

   (iii) NUMBER OF SEQUENCES: 34


(2) INFORMATION FOR SEQ ID NO:1:

     (i) SEQUENCE CHARACTERISTICS:
          (A) LENGTH: 1420 base pairs
          (B) TYPE: nucleic acid
          (C) STRANDEDNESS: both
```

-continued

```
          (D) TOPOLOGY: linear

    (ii) MOLECULE TYPE: cDNA

    (ix) FEATURE:
          (A) NAME/KEY: CDS
          (B) LOCATION: 4..1176

    (ix) FEATURE:
          (A) NAME/KEY: misc_feature
          (B) LOCATION: 4..24
          (D) OTHER INFORMATION: /product= "poly-His_Tag"

    (xi) SEQUENCE DESCRIPTION: SEQ ID NO:1:

CAT ATG CAC CAC CAT CAC CAT CAC TCA AAC GTG CGA GTG TCT AAC GGG       48
    Met His His His His His His Ser Asn Val Arg Val Ser Asn Gly
      1               5                  10                  15

AGC CCT AGC CTG GAG CGG ATG GAC GCC AGG CAG GCG GAG CAC CCC AAG       96
Ser Pro Ser Leu Glu Arg Met Asp Ala Arg Gln Ala Glu His Pro Lys
                 20                  25                  30

CCC TCG GCC TGC AGG AAC CTC TTC GGC CCG GTG GAC CAC GAA GAG TTA      144
Pro Ser Ala Cys Arg Asn Leu Phe Gly Pro Val Asp His Glu Glu Leu
             35                  40                  45

ACC CGG GAC TTG GAG AAG CAC TGC AGA GAC ATG GAA GAG GCG AGC CAG      192
Thr Arg Asp Leu Glu Lys His Cys Arg Asp Met Glu Glu Ala Ser Gln
         50                  55                  60

CGC AAG TGG AAT TTC GAT TTT CAG AAT CAC AAA CCC CTA GAG GGC AAG      240
Arg Lys Trp Asn Phe Asp Phe Gln Asn His Lys Pro Leu Glu Gly Lys
     65                  70                  75

TAC GAG TGG CAA GAG GTG GAG AAG GGC AGC TTG CCC GAG TTC TAC TAC      288
Tyr Glu Trp Gln Glu Val Glu Lys Gly Ser Leu Pro Glu Phe Tyr Tyr
 80                  85                  90                  95

AGA CCC CCG CGG CCC CCC AAA GGT GCC TGC AAG GTG CCG GCG CAG GAG      336
Arg Pro Pro Arg Pro Pro Lys Gly Ala Cys Lys Val Pro Ala Gln Glu
                100                 105                 110

AGC CAG GAT GTC AGC GGG AGC CGC CCG GCG GCG CCT TTA ATT GGG GCT      384
Ser Gln Asp Val Ser Gly Ser Arg Pro Ala Ala Pro Leu Ile Gly Ala
            115                 120                 125

CCG GCT AAC TCT GAG GAC ACG CAT TTG GTG GAC CCA AAG ACT GAT CCG      432
Pro Ala Asn Ser Glu Asp Thr His Leu Val Asp Pro Lys Thr Asp Pro
        130                 135                 140

TCG GAC AGC CAG ACG GGG TTA GCG GAG CAA TGC GCA GGA ATA AGG AAG      480
Ser Asp Ser Gln Thr Gly Leu Ala Glu Gln Cys Ala Gly Ile Arg Lys
    145                 150                 155

CGA CCT GCA ACC GAC GAT TCT TCT ACT CAA AAC AAA AGA GCC AAC AGA      528
Arg Pro Ala Thr Asp Asp Ser Ser Thr Gln Asn Lys Arg Ala Asn Arg
160                 165                 170                 175

ACA GAA GAA AAT GTT TCA GAC GGT TCC CCA AAT GCC GGT TCT GTG GAG      576
Thr Glu Glu Asn Val Ser Asp Gly Ser Pro Asn Ala Gly Ser Val Glu
                180                 185                 190

CAG ACG CCC AAG AAG CCT GGC CTC AGA AGA CGT CAA ACG GGT GGC GGG      624
Gln Thr Pro Lys Lys Pro Gly Leu Arg Arg Arg Gln Thr Gly Gly Gly
            195                 200                 205

GGC AGC GGG GGT GGC GGT TCC GGC GGG GGT GGA TCC GAA TTC TGC GGC      672
Gly Ser Gly Gly Gly Gly Ser Gly Gly Gly Gly Ser Glu Phe Cys Gly
        210                 215                 220

CGC GCG TGC GCT CGG CGG CTG CGG AGA GGG GAG AGC ATG CAG CGG GCG      720
Arg Ala Cys Ala Arg Arg Leu Arg Arg Gly Glu Ser Met Gln Arg Ala
    225                 230                 235

GCG GGG AGC AGC ATG GAG CCT TCG GCT GAC TGG CTG GCC ACG GCC GCG      768
Ala Gly Ser Ser Met Glu Pro Ser Ala Asp Trp Leu Ala Thr Ala Ala
240                 245                 250                 255
```

-continued

```
GCC CGG GGT CGG GTA GAG GAG GTG CGG GCG CTG CTG GAG GCG GTG GCG      816
Ala Arg Gly Arg Val Glu Glu Val Arg Ala Leu Leu Glu Ala Val Ala
                260                 265                 270

CTG CCC AAC GCA CCG AAT AGT TAC GGT CGG AGG CCG ATC CAG GTC ATG      864
Leu Pro Asn Ala Pro Asn Ser Tyr Gly Arg Arg Pro Ile Gln Val Met
            275                 280                 285

ATG ATG GGC AGC GCC CGA GTG GCG GAG CTG CTG CTG CTC CAC GGC GCG      912
Met Met Gly Ser Ala Arg Val Ala Glu Leu Leu Leu Leu His Gly Ala
        290                 295                 300

GAG CCC AAC TGC GCC GAC CCC GCC ACT CTC ACC CGA CCC GTG CAC GAC      960
Glu Pro Asn Cys Ala Asp Pro Ala Thr Leu Thr Arg Pro Val His Asp
    305                 310                 315

GCT GCC CGG GAG GGC TTC CTG GAC ACG CTG GTG GTG CTG CAC CGG GCC     1008
Ala Ala Arg Glu Gly Phe Leu Asp Thr Leu Val Val Leu His Arg Ala
320                 325                 330                 335

GGG GCG CGG CTG GAC GTG CGC GAT GCC TGG GGC CGT CTG CCC GTG GAC     1056
Gly Ala Arg Leu Asp Val Arg Asp Ala Trp Gly Arg Leu Pro Val Asp
                340                 345                 350

CTG GCT GAG GAG CTG GGC CAT CGC GAT GTC GCA CGG TAC CTG CGC GCG     1104
Leu Ala Glu Glu Leu Gly His Arg Asp Val Ala Arg Tyr Leu Arg Ala
            355                 360                 365

GCT GCG GGG GGC ACC AGA GGC AGT AAC CAT GCC CGC ATA GAT GCC GCG     1152
Ala Ala Gly Gly Thr Arg Gly Ser Asn His Ala Arg Ile Asp Ala Ala
        370                 375                 380

GAA GGT CCC TCA GAC ATC CCC GAT TGAAAGAACC AGAGAGGCTC TGAGAAACCT    1206
Glu Gly Pro Ser Asp Ile Pro Asp
    385                 390

CGGGAAACTT AGATCATCAG TCACCGAAGG TCCTACAGGG CCACAACTGC CCCCGCCACA   1266

ACCCACCCCG CTTTCGTAGT TTTCATTTAG AAAATAGAGC TTTTAAAAAT GTCCTGCCTT   1326

TTAACGTAGA TATAAGCCTT CCCCCACTAC CGTAAATGTC CATTTATATC ATTTTTTATA   1386

TATTCTTATA AAAATGTAAA AAAGAAAACT CGAG                               1420
```

(2) INFORMATION FOR SEQ ID NO:2:

(i) SEQUENCE CHARACTERISTICS:
(A) LENGTH: 391 amino acids
(B) TYPE: amino acid
(D) TOPOLOGY: linear (ii) MOLECULE TYPE: protein (xi) SEQUENCE DESCRIPTION: SEQ ID NO:2:

```
Met His His His His His His Ser Asn Val Arg Val Ser Asn Gly Ser
  1               5                  10                  15

Pro Ser Leu Glu Arg Met Asp Ala Arg Gln Ala Glu His Pro Lys Pro
             20                  25                  30

Ser Ala Cys Arg Asn Leu Phe Gly Pro Val Asp His Glu Glu Leu Thr
         35                  40                  45

Arg Asp Leu Glu Lys His Cys Arg Asp Met Glu Glu Ala Ser Gln Arg
     50                  55                  60

Lys Trp Asn Phe Asp Phe Gln Asn His Lys Pro Leu Glu Gly Lys Tyr
 65                  70                  75                  80

Glu Trp Gln Glu Val Glu Lys Gly Ser Leu Pro Glu Phe Tyr Tyr Arg
                 85                  90                  95

Pro Pro Arg Pro Pro Lys Gly Ala Cys Lys Val Pro Ala Gln Glu Ser
            100                 105                 110

Gln Asp Val Ser Gly Ser Arg Pro Ala Ala Pro Leu Ile Gly Ala Pro
        115                 120                 125
```

-continued

```
Ala Asn Ser Glu Asp Thr His Leu Val Asp Pro Lys Thr Asp Pro Ser
    130                 135                 140

Asp Ser Gln Thr Gly Leu Ala Glu Gln Cys Ala Gly Ile Arg Lys Arg
145                 150                 155                 160

Pro Ala Thr Asp Asp Ser Ser Thr Gln Asn Lys Arg Ala Asn Arg Thr
                165                 170                 175

Glu Glu Asn Val Ser Asp Gly Ser Pro Asn Ala Gly Ser Val Glu Gln
            180                 185                 190

Thr Pro Lys Lys Pro Gly Leu Arg Arg Arg Gln Thr Gly Gly Gly Gly
        195                 200                 205

Ser Gly Gly Gly Gly Ser Gly Gly Gly Gly Ser Glu Phe Cys Gly Arg
    210                 215                 220

Ala Cys Ala Arg Arg Leu Arg Arg Gly Glu Ser Met Gln Arg Ala Ala
225                 230                 235                 240

Gly Ser Ser Met Glu Pro Ser Ala Asp Trp Leu Ala Thr Ala Ala Ala
                245                 250                 255

Arg Gly Arg Val Glu Glu Val Arg Ala Leu Leu Glu Ala Val Ala Leu
            260                 265                 270

Pro Asn Ala Pro Asn Ser Tyr Gly Arg Arg Pro Ile Gln Val Met Met
        275                 280                 285

Met Gly Ser Ala Arg Val Ala Glu Leu Leu Leu Leu His Gly Ala Glu
    290                 295                 300

Pro Asn Cys Ala Asp Pro Ala Thr Leu Thr Arg Pro Val His Asp Ala
305                 310                 315                 320

Ala Arg Glu Gly Phe Leu Asp Thr Leu Val Val Leu His Arg Ala Gly
                325                 330                 335

Ala Arg Leu Asp Val Arg Asp Ala Trp Gly Arg Leu Pro Val Asp Leu
            340                 345                 350

Ala Glu Glu Leu Gly His Arg Asp Val Ala Arg Tyr Leu Arg Ala Ala
        355                 360                 365

Ala Gly Gly Thr Arg Gly Ser Asn His Ala Arg Ile Asp Ala Ala Glu
    370                 375                 380

Gly Pro Ser Asp Ile Pro Asp
385                 390
```

(2) INFORMATION FOR SEQ ID NO:3:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:3:

```
GCGGCCGGTC ATATGCACCA CCATCACCAT CACTCAAACG TGCGAGTGTC T             51
```

(2) INFORMATION FOR SEQ ID NO:4:

(i) SEQUENCE CHARACTERISTICS:
(A) LENGTH: 96 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:4:

-continued

```
GCCGCCGGCG TCGACTCGGC CGAATTCGGA TCCACCCCCG CCGGAACCGC CACCCCCGCT      60

GCCCCCGCCA CCCGTTTGAC GTCTTCTGAG GCCAGG                               96
```

(2) INFORMATION FOR SEQ ID NO:5:

(i) SEQUENCE CHARACTERISTICS:
(A) LENGTH: 1143 base pairs
(B) TYPE: nucleic acid
(C) STRANDEDNESS: both
(D) TOPOLOGY: linear (ii) MOLECULE TYPE: cDNA (ix) FEATURE:
(A) NAME/KEY: CDS
(B) LOCATION: 1..1140

(xi) SEQUENCE DESCRIPTION: SEQ ID NO:5:

```
ATG GGA TAC CCT TAT GAT GTG CCA GAT TAT GCC GAT CCG GCG GCG GGG       48
Met Gly Tyr Pro Tyr Asp Val Pro Asp Tyr Ala Asp Pro Ala Ala Gly
  1               5                  10                  15

AGC AGC ATG GAG CCT TCG GCT GAC TGG CTG GCC ACG GCC GCG GCC CGG       96
Ser Ser Met Glu Pro Ser Ala Asp Trp Leu Ala Thr Ala Ala Ala Arg
             20                  25                  30

GGT CGG GTA GAG GAG GTG CGG GCG CTG CTG GAG GCG GGG GCG CTG CCC      144
Gly Arg Val Glu Glu Val Arg Ala Leu Leu Glu Ala Gly Ala Leu Pro
         35                  40                  45

AAC GCA CCG AAT AGT TAC GGT CGG AGG CCG ATC CAG GTC ATG ATG ATG      192
Asn Ala Pro Asn Ser Tyr Gly Arg Arg Pro Ile Gln Val Met Met Met
     50                  55                  60

GGC AGC GCC CGA GTG GCG GAG CTG CTG CTG CTC CAC GGC GCG GAG CCC      240
Gly Ser Ala Arg Val Ala Glu Leu Leu Leu Leu His Gly Ala Glu Pro
 65                  70                  75                  80

AAC TGC GCC GAC CCC GCC ACT CTC ACC CGA CCC GTG CAC GAC GCT GCC      288
Asn Cys Ala Asp Pro Ala Thr Leu Thr Arg Pro Val His Asp Ala Ala
                 85                  90                  95

CGG GAG GGC TTC CTG GAC ACG CTG GTG GTG CTG CAC CGG GCC GGG GCG      336
Arg Glu Gly Phe Leu Asp Thr Leu Val Val Leu His Arg Ala Gly Ala
            100                 105                 110

CGG CTG GAC GTG CGC GAT GCC TGG GGC CGT CTG CCC GTG GAC CTG GCT      384
Arg Leu Asp Val Arg Asp Ala Trp Gly Arg Leu Pro Val Asp Leu Ala
        115                 120                 125

GAG GAG CTG GGC CAT CGC GAT GTC GCA CGG TAC CTG CGC GCG GCT GCG      432
Glu Glu Leu Gly His Arg Asp Val Ala Arg Tyr Leu Arg Ala Ala Ala
    130                 135                 140

GGG GGC ACC AGA GGC AGT AAC CAT GCC CGC ATA GAT GCC GCG GAA GGT      480
Gly Gly Thr Arg Gly Ser Asn His Ala Arg Ile Asp Ala Ala Glu Gly
145                 150                 155                 160

CCC TCA GAC ATC CCC GAT GGT GGC GGG GGC AGC GGG GGT GGC GGT TCC      528
Pro Ser Asp Ile Pro Asp Gly Gly Gly Gly Ser Gly Gly Gly Gly Ser
                165                 170                 175

GGC GGG GGT GGA TCC GTC GAG TCA AAC GTG CGA GTG TCT AAC GGG CGC      576
Gly Gly Gly Gly Ser Val Glu Ser Asn Val Arg Val Ser Asn Gly Arg
            180                 185                 190

CCT AGC CTG GAG CGG ATG GAC GCC AGG CAG GCG GAG CAC CCC AAG CCC      624
Pro Ser Leu Glu Arg Met Asp Ala Arg Gln Ala Glu His Pro Lys Pro
        195                 200                 205

TCG GCC TGC AGG AAC CTC TTC GGC CCG GTG GAC CAC GAA GAG TTA ACC      672
Ser Ala Cys Arg Asn Leu Phe Gly Pro Val Asp His Glu Glu Leu Thr
    210                 215                 220

CGG GAC TTG GAG AAG CAC TGC AGA GAC ATG GAA GAG GCG AGC CAG CGC      720
```

-continued

```
Arg Asp Leu Glu Lys His Cys Arg Asp Met Glu Glu Ala Ser Gln Arg
225                 230                 235                 240

AAG TGG AAT TTC GAT TTT CAG AAT CAC AAA CCC CTA GAG GGC AAG TAC      768
Lys Trp Asn Phe Asp Phe Gln Asn His Lys Pro Leu Glu Gly Lys Tyr
                245                 250                 255

GAG TGG CAA GAG GTG GAG AAG GGC AGC TTG CCC GAG TTC TAC TAC AGA      816
Glu Trp Gln Glu Val Glu Lys Gly Ser Leu Pro Glu Phe Tyr Tyr Arg
            260                 265                 270

CCC CCG CGG CCC CCC AAA GGT GCC TGC AAG GTG CCG GCG CAG GAG AGC      864
Pro Pro Arg Pro Pro Lys Gly Ala Cys Lys Val Pro Ala Gln Glu Ser
        275                 280                 285

CAG GAT GTC AGC GGG AGC CGC CCG GCG GCG CCT TTA ATT GGG GCT CCG      912
Gln Asp Val Ser Gly Ser Arg Pro Ala Ala Pro Leu Ile Gly Ala Pro
    290                 295                 300

GCT AAC TCT GAG GAC ACG CAT TTG GTG GAC CCA AAG ACT GAT CCG TCG      960
Ala Asn Ser Glu Asp Thr His Leu Val Asp Pro Lys Thr Asp Pro Ser
305                 310                 315                 320

GAC AGC CAG ACG GGG TTA GCG GAG CAA TGC GCA GGA ATA AGG AAG CGA     1008
Asp Ser Gln Thr Gly Leu Ala Glu Gln Cys Ala Gly Ile Arg Lys Arg
                325                 330                 335

CCT GCA ACC GAC GAT TCT TCT ACT CAA AAC AAA AGA GCC AAC AGA ACA     1056
Pro Ala Thr Asp Asp Ser Ser Thr Gln Asn Lys Arg Ala Asn Arg Thr
            340                 345                 350

GAA GAA AAT GTT TCA GAC GGT TCC CCA AAT GCC GGT TCT GTG GAG CAG     1104
Glu Glu Asn Val Ser Asp Gly Ser Pro Asn Ala Gly Ser Val Glu Gln
        355                 360                 365

ACG CCC AAG AAG CCT GGC CTC AGA AGA CGT CAA ACG TAA                 1143
Thr Pro Lys Lys Pro Gly Leu Arg Arg Arg Gln Thr
    370                 375                 380
```

(2) INFORMATION FOR SEQ ID NO:6:

(i) SEQUENCE CHARACTERISTICS:
(A) LENGTH: 380 amino acids
(B) TYPE: amino acid
(D) TOPOLOGY: linear (ii) MOLECULE TYPE: protein (xi) SEQUENCE DESCRIPTION: SEQ ID NO:6:

```
Met Gly Tyr Pro Tyr Asp Val Pro Asp Tyr Ala Asp Pro Ala Ala Gly
  1               5                  10                  15

Ser Ser Met Glu Pro Ser Ala Asp Trp Leu Ala Thr Ala Ala Ala Arg
             20                  25                  30

Gly Arg Val Glu Glu Val Arg Ala Leu Leu Glu Ala Gly Ala Leu Pro
         35                  40                  45

Asn Ala Pro Asn Ser Tyr Gly Arg Arg Pro Ile Gln Val Met Met Met
     50                  55                  60

Gly Ser Ala Arg Val Ala Glu Leu Leu Leu Leu His Gly Ala Glu Pro
 65                  70                  75                  80

Asn Cys Ala Asp Pro Ala Thr Leu Thr Arg Pro Val His Asp Ala Ala
                 85                  90                  95

Arg Glu Gly Phe Leu Asp Thr Leu Val Val Leu His Arg Ala Gly Ala
            100                 105                 110

Arg Leu Asp Val Arg Asp Ala Trp Gly Arg Leu Pro Val Asp Leu Ala
        115                 120                 125

Glu Glu Leu Gly His Arg Asp Val Ala Arg Tyr Leu Arg Ala Ala Ala
    130                 135                 140

Gly Gly Thr Arg Gly Ser Asn His Ala Arg Ile Asp Ala Ala Glu Gly
```

-continued

```
145                 150                 155                 160

Pro Ser Asp Ile Pro Asp Gly Gly Gly Gly Ser Gly Gly Gly Gly Ser
                165                 170                 175

Gly Gly Gly Gly Ser Val Glu Ser Asn Val Arg Val Ser Asn Gly Arg
            180                 185                 190

Pro Ser Leu Glu Arg Met Asp Ala Arg Gln Ala Glu His Pro Lys Pro
        195                 200                 205

Ser Ala Cys Arg Asn Leu Phe Gly Pro Val Asp His Glu Glu Leu Thr
    210                 215                 220

Arg Asp Leu Glu Lys His Cys Arg Asp Met Glu Glu Ala Ser Gln Arg
225                 230                 235                 240

Lys Trp Asn Phe Asp Phe Gln Asn His Lys Pro Leu Glu Gly Lys Tyr
                245                 250                 255

Glu Trp Gln Glu Val Glu Lys Gly Ser Leu Pro Glu Phe Tyr Tyr Arg
            260                 265                 270

Pro Pro Arg Pro Pro Lys Gly Ala Cys Lys Val Pro Ala Gln Glu Ser
        275                 280                 285

Gln Asp Val Ser Gly Ser Arg Pro Ala Ala Pro Leu Ile Gly Ala Pro
    290                 295                 300

Ala Asn Ser Glu Asp Thr His Leu Val Asp Pro Lys Thr Asp Pro Ser
305                 310                 315                 320

Asp Ser Gln Thr Gly Leu Ala Glu Gln Cys Ala Gly Ile Arg Lys Arg
                325                 330                 335

Pro Ala Thr Asp Asp Ser Ser Thr Gln Asn Lys Arg Ala Asn Arg Thr
            340                 345                 350

Glu Glu Asn Val Ser Asp Gly Ser Pro Asn Ala Gly Ser Val Glu Gln
        355                 360                 365

Thr Pro Lys Lys Pro Gly Leu Arg Arg Arg Gln Thr
    370                 375                 380
```

(2) INFORMATION FOR SEQ ID NO:7:

(i) SEQUENCE CHARACTERISTICS:
(A) LENGTH: 1098 base pairs
(B) TYPE: nucleic acid
(C) STRANDEDNESS: both
(D) TOPOLOGY: linear (ii) MOLECULE TYPE: cDNA (ix) FEATURE:
(A) NAME/KEY: CDS
(B) LOCATION: 1..1095

(xi) SEQUENCE DESCRIPTION: SEQ ID NO:7:

```
ATG GGA TAC CCT TAT GAT GTG CCA GAT TAT GCC GAT CCG GCG GCG GGG        48
Met Gly Tyr Pro Tyr Asp Val Pro Asp Tyr Ala Asp Pro Ala Ala Gly
  1               5                  10                  15

AGC AGC ATG GAG CCT TCG GCT GAC TGG CTG GCC ACG GCC GCG GCC CGG        96
Ser Ser Met Glu Pro Ser Ala Asp Trp Leu Ala Thr Ala Ala Ala Arg
             20                  25                  30

GGT CGG GTA GAG GAG GTG CGG GCG CTG CTG GAG GCG GGG GCG CTG CCC       144
Gly Arg Val Glu Glu Val Arg Ala Leu Leu Glu Ala Gly Ala Leu Pro
         35                  40                  45

AAC GCA CCG AAT AGT TAC GGT CGG AGG CCG ATC CAG GTC ATG ATG ATG       192
Asn Ala Pro Asn Ser Tyr Gly Arg Arg Pro Ile Gln Val Met Met Met
     50                  55                  60

GGC AGC GCC CGA GTG GCG GAG CTG CTG CTG CTC CAC GGC GCG GAG CCC       240
Gly Ser Ala Arg Val Ala Glu Leu Leu Leu Leu His Gly Ala Glu Pro
```

-continued

```
 65                  70                  75                  80

AAC TGC GCC GAC CCC GCC ACT CTC ACC CGA CCC GTG CAC GAC GCT GCC      288
Asn Cys Ala Asp Pro Ala Thr Leu Thr Arg Pro Val His Asp Ala Ala
                 85                  90                  95

CGG GAG GGC TTC CTG GAC ACG CTG GTG GTG CTG CAC CGG GCC GGG GCG      336
Arg Glu Gly Phe Leu Asp Thr Leu Val Val Leu His Arg Ala Gly Ala
            100                 105                 110

CGG CTG GAC GTG CGC GAT GCC TGG GGC CGT CTG CCC GTG GAC CTG GCT      384
Arg Leu Asp Val Arg Asp Ala Trp Gly Arg Leu Pro Val Asp Leu Ala
        115                 120                 125

GAG GAG CTG GGC CAT CGC GAT GTC GCA CGG TAC CTG CGC GCG GCT GCG      432
Glu Glu Leu Gly His Arg Asp Val Ala Arg Tyr Leu Arg Ala Ala Ala
    130                 135                 140

GGG GGC ACC AGA GGC AGT AAC CAT GCC CGC ATA GAT GCC GCG GAA GGT      480
Gly Gly Thr Arg Gly Ser Asn His Ala Arg Ile Asp Ala Ala Glu Gly
145                 150                 155                 160

CCC TCA GAC ATC CCC GAT GTC GAG TCA AAC GTG CGA GTG TCT AAC GGG      528
Pro Ser Asp Ile Pro Asp Val Glu Ser Asn Val Arg Val Ser Asn Gly
                165                 170                 175

CGC CCT AGC CTG GAG CGG ATG GAC GCC AGG CAG GCG GAG CAC CCC AAG      576
Arg Pro Ser Leu Glu Arg Met Asp Ala Arg Gln Ala Glu His Pro Lys
            180                 185                 190

CCC TCG GCC TGC AGG AAC CTC TTC GGC CCG GTG GAC CAC GAA GAG TTA      624
Pro Ser Ala Cys Arg Asn Leu Phe Gly Pro Val Asp His Glu Glu Leu
        195                 200                 205

ACC CGG GAC TTG GAG AAG CAC TGC AGA GAC ATG GAA GAG GCG AGC CAG      672
Thr Arg Asp Leu Glu Lys His Cys Arg Asp Met Glu Glu Ala Ser Gln
    210                 215                 220

CGC AAG TGG AAT TTC GAT TTT CAG AAT CAC AAA CCC CTA GAG GGC AAG      720
Arg Lys Trp Asn Phe Asp Phe Gln Asn His Lys Pro Leu Glu Gly Lys
225                 230                 235                 240

TAC GAG TGG CAA GAG GTG GAG AAG GGC AGC TTG CCC GAG TTC TAC TAC      768
Tyr Glu Trp Gln Glu Val Glu Lys Gly Ser Leu Pro Glu Phe Tyr Tyr
                245                 250                 255

AGA CCC CCG CGG CCC CCC AAA GGT GCC TGC AAG GTG CCG GCG CAG GAG      816
Arg Pro Pro Arg Pro Pro Lys Gly Ala Cys Lys Val Pro Ala Gln Glu
            260                 265                 270

AGC CAG GAT GTC AGC GGG AGC CGC CCG GCG GCG CCT TTA ATT GGG GCT      864
Ser Gln Asp Val Ser Gly Ser Arg Pro Ala Ala Pro Leu Ile Gly Ala
        275                 280                 285

CCG GCT AAC TCT GAG GAC ACG CAT TTG GTG GAC CCA AAG ACT GAT CCG      912
Pro Ala Asn Ser Glu Asp Thr His Leu Val Asp Pro Lys Thr Asp Pro
    290                 295                 300

TCG GAC AGC CAG ACG GGG TTA GCG GAG CAA TGC GCA GGA ATA AGG AAG      960
Ser Asp Ser Gln Thr Gly Leu Ala Glu Gln Cys Ala Gly Ile Arg Lys
305                 310                 315                 320

CGA CCT GCA ACC GAC GAT TCT TCT ACT CAA AAC AAA AGA GCC AAC AGA     1008
Arg Pro Ala Thr Asp Asp Ser Ser Thr Gln Asn Lys Arg Ala Asn Arg
                325                 330                 335

ACA GAA GAA AAT GTT TCA GAC GGT TCC CCA AAT GCC GGT TCT GTG GAG     1056
Thr Glu Glu Asn Val Ser Asp Gly Ser Pro Asn Ala Gly Ser Val Glu
            340                 345                 350

CAG ACG CCC AAG AAG CCT GGC CTC AGA AGA CGT CAA ACG TAA             1098
Gln Thr Pro Lys Lys Pro Gly Leu Arg Arg Arg Gln Thr
        355                 360                 365
```

(2) INFORMATION FOR SEQ ID NO:8:

(i) SEQUENCE CHARACTERISTICS:
(A) LENGTH: 365 amino acids

-continued (B) TYPE: amino acid
(D) TOPOLOGY: linear (ii) MOLECULE TYPE: protein (xi) SEQUENCE DESCRIPTION: SEQ ID NO:8:

```
Met Gly Tyr Pro Tyr Asp Val Pro Asp Tyr Ala Asp Pro Ala Ala Gly
  1               5                  10                  15

Ser Ser Met Glu Pro Ser Ala Asp Trp Leu Ala Thr Ala Ala Ala Arg
            20                  25                  30

Gly Arg Val Glu Glu Val Arg Ala Leu Leu Glu Ala Gly Ala Leu Pro
        35                  40                  45

Asn Ala Pro Asn Ser Tyr Gly Arg Arg Pro Ile Gln Val Met Met Met
     50                  55                  60

Gly Ser Ala Arg Val Ala Glu Leu Leu Leu Leu His Gly Ala Glu Pro
 65                  70                  75                  80

Asn Cys Ala Asp Pro Ala Thr Leu Thr Arg Pro Val His Asp Ala Ala
                 85                  90                  95

Arg Glu Gly Phe Leu Asp Thr Leu Val Val Leu His Arg Ala Gly Ala
            100                 105                 110

Arg Leu Asp Val Arg Asp Ala Trp Gly Arg Leu Pro Val Asp Leu Ala
        115                 120                 125

Glu Glu Leu Gly His Arg Asp Val Ala Arg Tyr Leu Arg Ala Ala Ala
    130                 135                 140

Gly Gly Thr Arg Gly Ser Asn His Ala Arg Ile Asp Ala Ala Glu Gly
145                 150                 155                 160

Pro Ser Asp Ile Pro Asp Val Glu Ser Asn Val Arg Val Ser Asn Gly
                165                 170                 175

Arg Pro Ser Leu Glu Arg Met Asp Ala Arg Gln Ala Glu His Pro Lys
            180                 185                 190

Pro Ser Ala Cys Arg Asn Leu Phe Gly Pro Val Asp His Glu Glu Leu
        195                 200                 205

Thr Arg Asp Leu Glu Lys His Cys Arg Asp Met Glu Glu Ala Ser Gln
    210                 215                 220

Arg Lys Trp Asn Phe Asp Phe Gln Asn His Lys Pro Leu Glu Gly Lys
225                 230                 235                 240

Tyr Glu Trp Gln Glu Val Glu Lys Gly Ser Leu Pro Glu Phe Tyr Tyr
                245                 250                 255

Arg Pro Pro Arg Pro Pro Lys Gly Ala Cys Lys Val Pro Ala Gln Glu
            260                 265                 270

Ser Gln Asp Val Ser Gly Ser Arg Pro Ala Ala Pro Leu Ile Gly Ala
        275                 280                 285

Pro Ala Asn Ser Glu Asp Thr His Leu Val Asp Pro Lys Thr Asp Pro
    290                 295                 300

Ser Asp Ser Gln Thr Gly Leu Ala Glu Gln Cys Ala Gly Ile Arg Lys
305                 310                 315                 320

Arg Pro Ala Thr Asp Asp Ser Ser Thr Gln Asn Lys Arg Ala Asn Arg
                325                 330                 335

Thr Glu Glu Asn Val Ser Asp Gly Ser Pro Asn Ala Gly Ser Val Glu
            340                 345                 350

Gln Thr Pro Lys Lys Pro Gly Leu Arg Arg Arg Gln Thr
        355                 360                 365
```

(2) INFORMATION FOR SEQ ID NO:9:

-continued (i) SEQUENCE CHARACTERISTICS:
(A) LENGTH: 75 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:9:

```
CATATGGGTG GCTGCCGTGG CGATATGTTC GGTTGCGGTG CTCCTCCAAA AAAGAAGAGA     60

AAGGTAGCTG GATTC                                                      75
```

(2) INFORMATION FOR SEQ ID NO:10:

(i) SEQUENCE CHARACTERISTICS:
(A) LENGTH: 24 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:10:

```
Met Gly Gly Cys Arg Gly Asp Met Phe Gly Cys Gly Ala Pro Pro Lys
1               5                   10                  15

Lys Lys Arg Lys Val Ala Gly Phe
            20
```

(2) INFORMATION FOR SEQ ID NO:11:

(i) SEQUENCE CHARACTERISTICS:
(A) LENGTH: 225 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:11:

```
CATATGGAGC CAGTAGATCC TAGACTAGAG CCCTGGAAGC ATCCAGGAAG TCAGCCTAAA     60

ACTGCTTGTA CCAATTGCTA TTGTAAAAAG TGTTGCTTTC ATTGCCAAGT TTGTTTCATA    120

ACAAAAGCCC TTGGCATCTC CTATGGCAGG AAGAAGCGGA GACAGCGACG AAGACCTCCT    180

CAAGGCAGTC AGACTCATCA AGTTTCTCTA AGTAAGCAAG GATTC                    225
```

(2) INFORMATION FOR SEQ ID NO:12:

(i) SEQUENCE CHARACTERISTICS:
(A) LENGTH: 72 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:12:

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Pro Pro Gln Gly Ser Gln Thr
    50                  55                  60
```

-continued

```
His Gln Val Ser Leu Ser Lys Gln
65                  70
```

(2) INFORMATION FOR SEQ ID NO:13:

(i) SEQUENCE CHARACTERISTICS:
(A) LENGTH: 912 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:13:

```
CATATGACCT CTCGCCGCTC CGTGAAGTCG GGTCCGCGGG AGGTTCCGCG CGATGAGTAC     60

GAGGATCTGT ACTACACCCC GTCTTCAGGT ATGGCGAGTC CCGATAGTCC GCCTGACACC    120

TCCCGCCGTG GCGCCCTACA GACACGCTCG CGCCAGAGGG GCGAGGTCCG TTTCGTCCAG    180

TACGACGAGT CGGATTATGC CCTCTACGGG GGCTCGTCAT CCGAAGACGA CGAACACCCG    240

GAGGTCCCCC GGACGCGGCG TCCCGTTTCC GGGGCGGTTT TGTCCGGCCC GGGGCCTGCG    300

CGGGCGCCTC CGCCACCCGC TGGGTCCGGA GGGGCCGGAC GCACACCCAC CACCGCCCCC    360

CGGGCCCCCC GAACCCAGCG GGTGGCGACT AAGGCCCCCG CGGCCCCGGC GGCGGAGACC    420

ACCCGCGGCA GGAAATCGGC CCAGCCAGAA TCCGCCGCAC TCCCAGACGC CCCCGCGTCG    480

ACGGCGCCAA CCCGATCCAA GACACCCGCG CAGGGGCTGG CCAGAAAGCT GCACTTTAGC    540

ACCGCCCCCC CAAACCCCGA CGCGCCATGG ACCCCCCGGG TGGCCGGCTT TAACAAGCGC    600

GTCTTCTGCG CCGCGGTCGG GCGCCTGGCG GCCATGCATG CCCGGATGGC GGCGGTCCAG    660

CTCTGGGACA TGTCGCGTCC GCGCACAGAC GAAGACCTCA ACGAACTCCT TGGCATCACC    720

ACCATCCGCG TGACGGTCTG CGAGGGCAAA AACCTGCTTC AGCGCGCCAA CGAGTTGGTG    780

AATCCAGACG TGGTGCAGGA CGTCGACGCG GCCACGGCGA CTCGAGGGCG TTCTGCGGCG    840

TCGCGCCCCA CCGAGCGACC TCGAGCCCCA GCCCGCTCCG CTTCTCGCCC CAGACGGCCC    900

GTCGAGGAAT TC                                                        912
```

(2) INFORMATION FOR SEQ ID NO:14:

(i) SEQUENCE CHARACTERISTICS:
(A) LENGTH: 301 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:14:

```
Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95
```

-continued

```
Gly Pro Ala Arg Ala Pro Pro Pro Pro Ala Gly Ser Gly Gly Ala Gly
            100                 105                 110

Arg Thr Pro Thr Thr Ala Pro Arg Ala Pro Arg Thr Gly Arg Val Ala
        115                 120                 125

Thr Lys Ala Pro Ala Ala Pro Ala Ala Glu Thr Thr Arg Gly Arg Lys
    130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
        195                 200                 205

Ala Ala Met His Ala Arg Met Ala Ala Val Gln Leu Trp Asp Met Ser
    210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
            260                 265                 270

Thr Arg Gly Arg Ser Ala Ala Ser Arg Pro Thr Glu Arg Pro Arg Ala
        275                 280                 285

Pro Ala Arg Ser Ala Ser Arg Pro Arg Arg Pro Val Glu
    290                 295                 300
```

(2) INFORMATION FOR SEQ ID NO:15:

(i) SEQUENCE CHARACTERISTICS:
(A) LENGTH: 120 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:15:

```
CATATGGACG TCGACGCGGC CACGGCGACT CGAGGGCGTT CTGCGGCGTC GCGCCCCACC      60

GAGCGACCTC GAGCCCCAGC CCGCTCCGCT TCTCGCCCCA GACGGCCCGT CGAGGAATTC     120
```

(2) INFORMATION FOR SEQ ID NO:16:

(i) SEQUENCE CHARACTERISTICS:
(A) LENGTH: 37 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:16:

```
Met Asp Val Asp Ala Ala Thr Ala Thr Arg Gly Arg Ser Ala Ala Ser
1               5                   10                  15

Arg Pro Thr Glu Arg Pro Arg Ala Pro Ala Arg Ser Ala Ser Arg Pro
            20                  25                  30

Arg Arg Pro Val Glu
        35
```

-continued (2) INFORMATION FOR SEQ ID NO:17:

(i) SEQUENCE CHARACTERISTICS:
(A) LENGTH: 557 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:17:

```
GAATTCGCCG CCACCATGGG ATACCCTTAT GATGTGCCAG ATTATGCCAG CCTGGAGCGG     60

ATGGACGCCA GGCAGGCGGA GCACCCCAAG CCCTCGGCCT GCAGGAACCT CTTCGGCCCG    120

GTGGACCACG AAGAGTTAAC CCGGGACTTG GAGAAGCACT GCAGAGACAT GGAAGAGGCG    180

AGCCAGCGCA AGTGGAATTT CGATTTTCAG AATCACAAAC CCCTAGAGGG CAAGTACGAG    240

TGGCAAGAGG TGGAGAAGGG CAGCTTGCCC GAGTTCTACT ACAGACCCCC GCGGCCCCCC    300

AAAGGTGCCT GCAAGGTGCC GGCGCAGGAG AGCCAGGATG TCAGCGGGAG CCGCCCGGCG    360

GCGCCTTTAA TTGGGGCTCC GGCTAACTCT GAGGACACGC ATTTGGTGGA CCCAAAGACT    420

GATCCGTCGG ACAGCCAGAC GGGGTTAGCG GAGCAATGCG CAGGAATAAG GAAGCGACCT    480

GCAACCGACG ATTCTTCTAC TCAAAACAAA AGAGCCAACA GAACAGAAGA AAATGTTTCA    540

GACGGTTAGG CGGCCGC                                                   557
```

(2) INFORMATION FOR SEQ ID NO:18:

(i) SEQUENCE CHARACTERISTICS:
(A) LENGTH: 167 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:18:

```
Met Ser Leu Glu Arg Met Asp Ala Arg Gln Ala Glu His Pro Lys Pro
1               5                   10                  15

Ser Ala Cys Arg Asn Leu Phe Gly Pro Val Asp His Glu Glu Leu Thr
            20                  25                  30

Arg Asp Leu Glu Lys His Cys Arg Asp Met Glu Glu Ala Ser Gln Arg
        35                  40                  45

Lys Trp Asn Phe Asp Phe Gln Asn His Lys Pro Leu Glu Gly Lys Tyr
    50                  55                  60

Glu Trp Gln Glu Val Glu Lys Gly Ser Leu Pro Glu Phe Tyr Tyr Arg
65                  70                  75                  80

Pro Pro Arg Pro Pro Lys Gly Ala Cys Lys Val Pro Ala Gln Glu Ser
                85                  90                  95

Gln Asp Val Ser Gly Ser Arg Pro Ala Ala Pro Leu Ile Gly Ala Pro
            100                 105                 110

Ala Asn Ser Glu Asp Thr His Leu Val Asp Pro Lys Thr Asp Pro Ser
        115                 120                 125

Asp Ser Gln Thr Gly Leu Ala Glu Gln Cys Ala Gly Ile Arg Lys Arg
    130                 135                 140

Pro Ala Thr Asp Asp Ser Ser Thr Gln Asn Lys Arg Ala Asn Arg Thr
145                 150                 155                 160

Glu Glu Asn Val Ser Asp Gly
                165
```

(2) INFORMATION FOR SEQ ID NO:19:

(i) SEQUENCE CHARACTERISTICS:
(A) LENGTH: 266 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:19:

```
GAATTCGCCG CCACCATGGG ATACCCTTAT GATGTGCCAG ATTATGCCAA GCCCTCGGCC     60

TGCAGGAACC TCTTCGGCCC GGTGGACCAC GAAGAGTTAA CCCGGGACTT GGAGAAGCAC    120

TGCAGAGACA TGGAAGAGGC GAGCCAGCGC AAGTGGAATT TCGATTTTCA GAATCACAAA    180

CCCCTAGAGG GCAAGTACGA GTGGCAAGAG GTGGAGAAGG GCAGCTTGCC CGAGTTCTAC    240

TACAGACCCC CGCGGTAGGC GGCCGC                                         266
```

(2) INFORMATION FOR SEQ ID NO:20:

(i) SEQUENCE CHARACTERISTICS:
(A) LENGTH: 70 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:20:

```
Met Lys Pro Ser Ala Cys Arg Asn Leu Phe Gly Pro Val Asp His Glu
1               5                   10                  15

Glu Leu Thr Arg Asp Leu Glu Lys His Cys Arg Asp Met Glu Glu Ala
            20                  25                  30

Ser Gln Arg Lys Trp Asn Phe Asp Phe Gln Asn His Lys Pro Leu Glu
        35                  40                  45

Gly Lys Tyr Glu Trp Gln Glu Val Glu Lys Gly Ser Leu Pro Glu Phe
    50                  55                  60

Tyr Tyr Arg Pro Pro Arg
65                  70
```

(2) INFORMATION FOR SEQ ID NO:21:

(i) SEQUENCE CHARACTERISTICS:
(A) LENGTH: 1028 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:21:

```
GAATTCGCCG CCACCATGGG ATACCCTTAT GATGTGCCAG ATTATGCCAG CCTGGAGCGG     60

ATGGACGCCA GGCAGGCGGA GCACCCCAAG CCCTCGGCCT GCAGGAACCT CTTCGGCCCG    120

GTGGACCACG AAGAGTTAAC CCGGGACTTG GAGAAGCACT GCAGAGACAT GGAAGAGGCG    180

AGCCAGCGCA AGTGGAATTT CGATTTTCAG AATCACAAAC CCCTAGAGGG CAAGTACGAG    240

TGGCAAGAGG TGGAGAAGGG CAGCTTGCCC GAGTTCTACT ACAGACCCCC GCGGCCCCCC    300

AAAGGTGCCT GCAAGGTGCC GGCGCAGGAG AGCCAGGATG TCAGCGGGAG CCGCCCGGCG    360

GCGCCTTTAA TTGGGGCTCC GGCTAACTCT GAGGACACGC ATTTGGTGGA CCCAAAGACT    420

GATCCGTCGG ACAGCCAGAC GGGGTTAGCG GAGCAATGCG CAGGAATAAG GAAGCGACCT    480
```

-continued

```
GCAACCGACG ATTCTTCTAC TCAAAACAAA AGAGCCAACA GAACAGAAGA AAATGTTTCA    540

GACGGTGTCG AGGATCCGGC GGCGGGGAGC AGCATGGAGC CTTCGGCTGA CTGGCTGGCC    600

ACGGCCGCGG CCCGGGGTCG GGTAGAGGAG GTGCGGGCGC TGCTGGAGGC GGGGGCGCTG    660

CCCAACGCAC CGAATAGTTA CGGTCGGAGG CCGATCCAGG TCATGATGAT GGGCAGCGCC    720

CGAGTGGCGG AGCTGCTGCT GCTCCACGGC GCGGAGCCCA ACTGCGCCGA CCCCGCCACT    780

CTCACCCGAC CCGTGCACGA CGCTGCCCGG GAGGGCTTCC TGGACACGCT GGTGGTGCTG    840

CACCGGGCCG GGGCGCGGCT GGACGTGCGC GATGCCTGGG GCCGTCTGCC CGTGGACCTG    900

GCTGAGGAGC TGGGCCATCG CGATGTCGCA CGGTACCTGC GCGCGGCTGC GGGGGGCACC    960

AGAGGCAGTA ACCATGCCCG CATAGATGCC GCGGAAGGTC CCTCAGACAT CCCCGATTGA   1020

GCGGCCGC                                                            1028
```

(2) INFORMATION FOR SEQ ID NO:22:

(i) SEQUENCE CHARACTERISTICS:
(A) LENGTH: 334 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:22:

```
Met Gly Tyr Pro Tyr Asp Val Pro Asp Tyr Ala Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Val Glu Asp Pro Ala Ala Gly Ser Ser Met Glu Pro Ser Ala Asp
            180                 185                 190

Trp Leu Ala Thr Ala Ala Ala Arg Gly Arg Val Glu Glu Val Arg Ala
        195                 200                 205

Leu Leu Glu Ala Gly Ala Leu Pro Asn Ala Pro Asn Ser Tyr Gly Arg
    210                 215                 220

Arg Pro Ile Gln Val Met Met Met Gly Ser Ala Arg Val Ala Glu Leu
225                 230                 235                 240

Leu Leu Leu His Gly Ala Glu Pro Asn Cys Ala Asp Pro Ala Thr Leu
```

-continued

```
                245                 250                 255

Thr Arg Pro Val His Asp Ala Ala Arg Glu Gly Phe Leu Asp Thr Leu
            260                 265                 270

Val Val Leu His Arg Ala Gly Ala Arg Leu Asp Val Arg Asp Ala Trp
        275                 280                 285

Gly Arg Leu Pro Val Asp Leu Ala Glu Glu Leu Gly His Arg Asp Val
    290                 295                 300

Ala Arg Tyr Leu Arg Ala Ala Ala Gly Gly Thr Arg Gly Ser Asn His
305                 310                 315                 320

Ala Arg Ile Asp Ala Ala Glu Gly Pro Ser Asp Ile Pro Asp
                325                 330
```

(2) INFORMATION FOR SEQ ID NO:23:

(i) SEQUENCE CHARACTERISTICS:
(A) LENGTH: 1073 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:23:

```
GAATTCGCCG CCACCATGGG ATACCCTTAT GATGTGCCAG ATTATGCCAG CCTGGAGCGG     60

ATGGACGCCA GGCAGGCGGA GCACCCCAAG CCCTCGGCCT GCAGGAACCT CTTCGGCCCG    120

GTGGACCACG AAGAGTTAAC CCGGGACTTG GAGAAGCACT GCAGAGACAT GGAAGAGGCG    180

AGCCAGCGCA AGTGGAATTT CGATTTTCAG AATCACAAAC CCCTAGAGGG CAAGTACGAG    240

TGGCAAGAGG TGGAGAAGGG CAGCTTGCCC GAGTTCTACT ACAGACCCCC GCGGCCCCCC    300

AAAGGTGCCT GCAAGGTGCC GGCGCAGGAG AGCCAGGATG TCAGCGGGAG CCGCCCGGCG    360

GCGCCTTTAA TTGGGGCTCC GGCTAACTCT GAGGACACGC ATTTGGTGGA CCCAAAGACT    420

GATCCGTCGG ACAGCCAGAC GGGGTTAGCG GAGCAATGCG CAGGAATAAG GAAGCGACCT    480

GCAACCGACG ATTCTTCTAC TCAAAACAAA AGAGCCAACA GAACAGAAGA AAATGTTTCA    540

GACGGTGGTG GCGGGGGCAG CGGGGGTGGC GGTTCCGGCG GGGGTGGATC CGTCGAGGAT    600

CCGGCGGCGG GGAGCAGCAT GGAGCCTTCG GCTGACTGGC TGGCCACGGC CGCGGCCCGG    660

GGTCGGGTAG AGGAGGTGCG GGCGCTGCTG GAGGCGGGGG CGCTGCCCAA CGCACCGAAT    720

AGTTACGGTC GGAGGCCGAT CCAGGTCATG ATGATGGGCA GCGCCCGAGT GGCGGAGCTG    780

CTGCTGCTCC ACGGCGCGGA GCCCAACTGC GCCGACCCCG CCACTCTCAC CCGACCCGTG    840

CACGACGCTG CCCGGGAGGG CTTCCTGGAC ACGCTGGTGG TGCTGCACCG GGCCGGGGCG    900

CGGCTGGACG TGCGCGATGC CTGGGGCCGT CTGCCCGTGG ACCTGGCTGA GGAGCTGGGC    960

CATCGCGATG TCGCACGGTA CCTGCGCGCG GCTGCGGGGG GCACCAGAGG CAGTAACCAT   1020

GCCCGCATAG ATGCCGCGGA AGGTCCCTCA GACATCCCCG ATTGAGCGGC CGC          1073
```

(2) INFORMATION FOR SEQ ID NO:24:

(i) SEQUENCE CHARACTERISTICS:
(A) LENGTH: 348 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:24:

-continued

```
Met Gly Tyr Pro Tyr Asp Val Pro Asp Tyr Ala Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Gly Gly Gly Gly Ser Gly Gly Gly Gly Ser Gly Gly Gly Gly Ser
            180                 185                 190

Val Glu Asp Pro Ala Ala Gly Ser Ser Met Glu Pro Ser Ala Asp Trp
        195                 200                 205

Leu Ala Thr Ala Ala Ala Arg Gly Arg Val Glu Glu Val Arg Ala Leu
    210                 215                 220

Leu Glu Ala Gly Ala Leu Pro Asn Ala Pro Asn Ser Tyr Gly Arg Arg
225                 230                 235                 240

Pro Ile Gln Val Met Met Met Gly Ser Ala Arg Val Ala Glu Leu Leu
                245                 250                 255

Leu Leu His Gly Ala Glu Pro Asn Cys Ala Asp Pro Ala Thr Leu Thr
            260                 265                 270

Arg Pro Val His Asp Ala Ala Arg Glu Gly Phe Leu Asp Thr Leu Val
        275                 280                 285

Val Leu His Arg Ala Gly Ala Arg Leu Asp Val Arg Asp Ala Trp Gly
    290                 295                 300

Leu Pro Val Asp Leu Ala Glu Glu Leu Gly His Arg Asp Val Ala Arg
305                 310                 315                 320

Tyr Leu Arg Ala Ala Ala Gly Gly Thr Arg Gly Ser Asn His Ala Arg
                325                 330                 335

Ile Asp Ala Ala Glu Gly Pro Ser Asp Ile Pro Asp
            340                 345
```

(2) INFORMATION FOR SEQ ID NO:25:

(i) SEQUENCE CHARACTERISTICS:
(A) LENGTH: 737 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:25:

-continued

```
GAATTCGCCG CCACCATGGG ATACCCTTAT GATGTGCCAG ATTATGCCAA GCCCTCGGCC    60

TGCAGGAACC TCTTCGGCCC GGTGGACCAC GAAGAGTTAA CCCGGGACTT GGAGAAGCAC   120

TGCAGAGACA TGGAAGAGGC GAGCCAGCGC AAGTGGAATT TCGATTTTCA GAATCACAAA   180

CCCCTAGAGG GCAAGTACGA GTGGCAAGAG GTGGAGAAGG GCAGCTTGCC CGAGTTCTAC   240

TACAGACCCC CGCGGGTCGA GGATCCGGCG GCGGGGAGCA GCATGGAGCC TTCGGCTGAC   300

TGGCTGGCCA CGGCCGCGGC CCGGGGTCGG GTAGAGGAGG TGCGGGCGCT GCTGGAGGCG   360

GGGGCGCTGC CCAACGCACC GAATAGTTAC GGTCGGAGGC CGATCCAGGT CATGATGATG   420

GGCAGCGCCC GAGTGGCGGA GCTGCTGCTG CTCCACGGCG CGGAGCCCAA CTGCGCCGAC   480

CCCGCCACTC TCACCCGACC CGTGCACGAC GCTGCCCGGG AGGGCTTCCT GGACACGCTG   540

GTGGTGCTGC ACCGGGCCGG GGCGCGGCTG GACGTGCGCG ATGCCTGGGG CCGTCTGCCC   600

GTGGACCTGG CTGAGGAGCT GGGCCATCGC GATGTCGCAC GGTACCTGCG CGCGGCTGCG   660

GGGGGCACCA GAGGCAGTAA CCATGCCCGC ATAGATGCCG CGGAAGGTCC CTCAGACATC   720

CCCGATTGAG CGGCCGC                                                  737
```

(2) INFORMATION FOR SEQ ID NO:26:

(i) SEQUENCE CHARACTERISTICS:
(A) LENGTH: 237 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:26:

```
Met Gly Tyr Pro Tyr Asp Val Pro Asp Tyr Ala Lys Pro Ser Ala Cys
1               5                   10                  15

Arg Asn Leu Phe Gly Pro Val Asp His Glu Glu Leu Thr Arg Asp Leu
            20                  25                  30

Glu Lys His Cys Arg Asp Met Glu Glu Ala Ser Gln Arg Lys Trp Asn
        35                  40                  45

Phe Asp Phe Gln Asn His Lys Pro Leu Glu Gly Lys Tyr Glu Trp Gln
    50                  55                  60

Glu Val Glu Lys Gly Ser Leu Pro Glu Phe Tyr Tyr Arg Pro Pro Arg
65                  70                  75                  80

Val Glu Asp Pro Ala Ala Gly Ser Ser Met Glu Pro Ser Ala Asp Trp
                85                  90                  95

Leu Ala Thr Ala Ala Ala Arg Gly Arg Val Glu Glu Val Arg Ala Leu
            100                 105                 110

Leu Glu Ala Gly Ala Leu Pro Asn Ala Pro Asn Ser Tyr Gly Arg Arg
        115                 120                 125

Pro Ile Gln Val Met Met Met Gly Ser Ala Arg Val Ala Glu Leu Leu
    130                 135                 140

Leu Leu His Gly Ala Glu Pro Asn Cys Ala Asp Pro Ala Thr Leu Thr
145                 150                 155                 160

Arg Pro Val His Asp Ala Ala Arg Glu Gly Phe Leu Asp Thr Leu Val
                165                 170                 175

Val Leu His Arg Ala Gly Ala Arg Leu Asp Val Arg Asp Ala Trp Gly
            180                 185                 190

Arg Leu Pro Val Asp Leu Ala Glu Glu Leu Gly His Arg Asp Val Ala
        195                 200                 205

Arg Tyr Leu Arg Ala Ala Ala Gly Gly Thr Arg Gly Ser Asn His Ala
```

-continued

```
    210                 215                 220

Arg Ile Asp Ala Ala Glu Gly Pro Ser Asp Ile Pro Asp
225                 230                 235
```

(2) INFORMATION FOR SEQ ID NO:27:

(i) SEQUENCE CHARACTERISTICS:
(A) LENGTH: 782 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:27:

```
GAATTCGCCG CCACCATGGG ATACCCTTAT GATGTGCCAG ATTATGCCAA GCCCTCGGCC     60

TGCAGGAACC TCTTCGGCCC GGTGGACCAC GAAGAGTTAA CCCGGGACTT GGAGAAGCAC    120

TGCAGAGACA TGGAAGAGGC GAGCCAGCGC AAGTGGAATT TCGATTTTCA GAATCACAAA    180

CCCCTAGAGG GCAAGTACGA GTGGCAAGAG GTGGAGAAGG GCAGCTTGCC CGAGTTCTAC    240

TACAGACCCC CGCGGGGTGG CGGGGGCAGC GGGGGTGGCG GTTCCGGCGG GGGTGGATCC    300

GTCGAGGATC CGGCGGCGGG GAGCAGCATG GAGCCTTCGG CTGACTGGCT GGCCACGGCC    360

GCGGCCCGGG GTCGGGTAGA GGAGGTGCGG GCGCTGCTGG AGGCGGGGGC GCTGCCCAAC    420

GCACCGAATA GTTACGGTCG GAGGCCGATC CAGGTCATGA TGATGGGCAG CGCCCGAGTG    480

GCGGAGCTGC TGCTGCTCCA CGGCGCGGAG CCCAACTGCG CCGACCCCGC CACTCTCACC    540

CGACCCGTGC ACGACGCTGC CCGGGAGGGC TTCCTGGACA CGCTGGTGGT GCTGCACCGG    600

GCCGGGGCGC GGCTGGACGT GCGCGATGCC TGGGGCCGTC TGCCCGTGGA CCTGGCTGAG    660

GAGCTGGGCC ATCGCGATGT CGCACGGTAC CTGCGCGCGG CTGCGGGGGG CACCAGAGGC    720

AGTAACCATG CCCGCATAGA TGCCGCGGAA GGTCCCTCAG ACATCCCCGA TTGAGCGGCC    780

GC                                                                   782
```

(2) INFORMATION FOR SEQ ID NO:28:

(i) SEQUENCE CHARACTERISTICS:
(A) LENGTH: 252 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:28:

```
Met Gly Tyr Pro Tyr Asp Val Pro Asp Tyr Ala Lys Pro Ser Ala Cys
1               5                   10                  15

Arg Asn Leu Phe Gly Pro Val Asp His Glu Glu Leu Thr Arg Asp Leu
            20                  25                  30

Glu Lys His Cys Arg Asp Met Glu Glu Ala Ser Gln Arg Lys Trp Asn
        35                  40                  45

Phe Asp Phe Gln Asn His Lys Pro Leu Glu Gly Lys Tyr Glu Trp Gln
    50                  55                  60

Glu Val Glu Lys Gly Ser Leu Pro Glu Phe Tyr Tyr Arg Pro Pro Arg
65                  70                  75                  80

Gly Gly Gly Gly Ser Gly Gly Gly Gly Ser Gly Gly Gly Gly Ser Val
                85                  90                  95

Glu Asp Pro Ala Ala Gly Ser Ser Met Glu Pro Ser Ala Asp Trp Leu
            100                 105                 110
```

-continued

```
Ala Thr Ala Ala Ala Arg Gly Arg Val Glu Glu Val Arg Ala Leu Leu
        115                 120                 125

Glu Ala Gly Ala Leu Pro Asn Ala Pro Asn Ser Tyr Gly Arg Arg Pro
    130                 135                 140

Ile Gln Val Met Met Met Gly Ser Ala Arg Val Ala Glu Leu Leu Leu
145                 150                 155                 160

Leu His Gly Ala Glu Pro Asn Cys Ala Asp Pro Ala Thr Leu Thr Arg
                165                 170                 175

Pro Val His Asp Ala Ala Arg Glu Gly Phe Leu Asp Thr Leu Val Val
            180                 185                 190

Leu His Arg Ala Gly Ala Arg Leu Asp Val Arg Asp Ala Trp Gly Arg
        195                 200                 205

Leu Pro Val Asp Leu Ala Glu Glu Leu Gly His Arg Asp Val Ala Arg
    210                 215                 220

Tyr Leu Arg Ala Ala Ala Gly Gly Thr Arg Gly Ser Asn His Ala Arg
225                 230                 235                 240

Ile Asp Ala Ala Glu Gly Pro Ser Asp Ile Pro Asp
                245                 250
```

(2) INFORMATION FOR SEQ ID NO:29:

(i) SEQUENCE CHARACTERISTICS:
(A) LENGTH: 26 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:29:

```
Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser
            20                  25
```

(2) INFORMATION FOR SEQ ID NO:30:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:30:

```
Cys Met His Ile Glu Ser Leu Asp Ser Tyr Thr Cys
1               5                   10
```

(2) INFORMATION FOR SEQ ID NO:31:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:31:

```
Cys Met Tyr Ile Glu Ala Leu Asp Lys Tyr Ala Cys
1               5                   10
```

-continued

```
(2) INFORMATION FOR SEQ ID NO:32:

     (i) SEQUENCE CHARACTERISTICS:
          (A) LENGTH: 32 amino acids
          (B) TYPE: amino acid
          (C) STRANDEDNESS:
          (D) TOPOLOGY: linear

    (ii) MOLECULE TYPE: peptide

    (xi) SEQUENCE DESCRIPTION: SEQ ID NO:32:

Xaa Xaa Xaa Glu Ala Ala Leu Ala Glu Ala Leu Ala Glu Ala Leu Ala
1               5                   10                  15

Glu Ala Leu Ala Glu Ala Leu Ala Glu Ala Leu Glu Ala Leu Ala Ala
            20                  25                  30


(2) INFORMATION FOR SEQ ID NO:33:

     (i) SEQUENCE CHARACTERISTICS:
          (A) LENGTH: 8 amino acids
          (B) TYPE: amino acid
          (C) STRANDEDNESS:
          (D) TOPOLOGY: linear

    (ii) MOLECULE TYPE: peptide

    (xi) SEQUENCE DESCRIPTION: SEQ ID NO:33:

Gly Asn Ala Ala Ala Ala Arg Arg
1               5


(2) INFORMATION FOR SEQ ID NO:34:

     (i) SEQUENCE CHARACTERISTICS:
          (A) LENGTH: 10 amino acids
          (B) TYPE: amino acid
          (C) STRANDEDNESS:
          (D) TOPOLOGY: linear

    (ii) MOLECULE TYPE: peptide

    (xi) SEQUENCE DESCRIPTION: SEQ ID NO:34:

Cys Asp Pro Gly Tyr Ile Gly Ser Arg Cys
1               5                   10
```